United States Patent [19]

Bennett et al.

[11] Patent Number: 5,624,899

[45] Date of Patent: Apr. 29, 1997

[54] METHOD FOR USING HTK LIGAND

[75] Inventors: Brian D. Bennett, Pacifica; William Matthews, Woodside, both of Calif.

[73] Assignee: Genentech Inc., So. San Francisco, Calif.

[21] Appl. No.: 436,044

[22] Filed: May 5, 1995

Related U.S. Application Data

[62] Division of Ser. No. 277,722, Jul. 20, 1994.
[51] Int. Cl.$^6$ .................................................. A61K 38/17
[52] U.S. Cl. ............................... 514/12; 514/2; 530/350
[58] Field of Search ......................... 514/2, 12; 435/69.1

[56] References Cited

FOREIGN PATENT DOCUMENTS

| | | |
|---|---|---|
| WO93/15201 | 8/1993 | WIPO . |
| WO95/27060 | 10/1995 | WIPO . |
| WO95/27061 | 10/1995 | WIPO . |
| WO96/01839 | 1/1996 | WIPO . |

OTHER PUBLICATIONS

Davis et al., *Science* vol. 266, pp. 816–819, 1994.

Andres et al., "Expression of two novel eph–related receptor protein tyrosine kinases in mammary gland development and carcinogenesis" *Oncogene* 9:1461–1467 (1994).

Bartley et al., "B61 is a ligand for the ECK receptor protein–tyrosine kinase" *Nature* 368:558–560 (Apr. 7, 1994).

Bennett, B.D. et al., "Cloning and characterization of HTK, a novel transmembrane tyrosine kinase of the EPH subfamily" *Journal of Biological Chemistry* 269(19):14211–14218 (1994).

Holzman et al., "A novel immediate–early response gene of endothelium is induced by cytokines and encodes a secreted protein" *Molecular & Cellular Biology* 10(11):5830–5838 (1990).

Lyman et al., "Molecular cloning of a ligand for the flt3/flk–2 tyrosine kinase receptor: a proliferative factor for primitive hematopoietic cells" *Cell* 75:1157–1167 (1993).

Beckmann et al., "Molecular characterization of a family of ligands for eph–related tyrosine kinase receptors" *EMBO Journal* 13(16):3757–3762 (1994).

Beckmann et al., "Molecular Characterization of a Family of Ligands for Eph–related Tyrosine Kinases" *Journal of Cellular Biochemistry Supplement O* (18 Part A) (Abstract Only) pp. E301(1994).

Bennett et al., "Molecular Cloning of a Ligand for the EPH–related Receptor Protein Tyrosine Kinase –Htk" *Blood* (abstract No. 1693) 84(10):427a (Nov. 15, 1994).

Bennett et al., "Molecular Cloning of a Ligand for the EPH–Related Receptor Protein–Tyrosine Kinase Htk" *Proc. Natl. Acad. Sci. USA* 92:1866–1870 (1995).

Bergemann et al., "ELF–2, a New Member of the Eph Ligand Family, Is Segmentally Expressed in Mouse Embryos in the Region of the Hindbrain and Newly Forming Somites" *Molecular & Cellular Biology* 15(9):4921–4929 (1995).

Bonaldo et al., "Human expressed sequence tag for chromosome 13, 5' end of clone 17" *GenBank* (Release 87) (Feb. 1995).

Bonaldo, M. et al., "Human expressed sequence tag for chromosome 13, 3' end of clone 18" *GenBank* (Release 87) (Feb. 1995).

Cerretti et al., "Isolation of Lerk–5: A Ligand of the EPH–related Receptor Tyrosine Kinases" *Molecular Immunology* 32(16):1197–1205 (1995).

Kozlosky et al., "Ligands for the Receptor Tyrosine Kinases hek and elk: Isolation of cDNAs Encoding a Family of Proteins" *Oncogene* 10:299–306 (1995).

*Primary Examiner*—Donald E. Adams
*Assistant Examiner*—Stephen Gucker
*Attorney, Agent, or Firm*—Walter H. Dreger

[57] ABSTRACT

A novel hepatoma transmembrane kinase receptor ligand (Htk ligand) which binds to, and activates, the Htk receptor is disclosed. As examples, mouse and human Htk ligands have been identified in a variety of tissues using a soluble Htk-Fc fusion protein. The ligands have been cloned and sequenced. The invention also relates to nucleic acids encoding the ligand, methods for production and use of the ligand, and antibodies directed thereto.

2 Claims, 11 Drawing Sheets

```
  1 CCCACGGGTCCGCGCGGCTGAGGGACGGCAGGGTGAGCGCACCTGGCCTCCGGCCCCGGAGGATTGGGGT
                                                       M A M A R S R R D S V W K Y
                                                                           10
101 CGCTGCCCGCGGCCCGGTCCCAACGCGTCCCGGAGTGCGCAGAACTGGGAGCGGCTTGGGCATGGCCGCTTCCAGGAGGACTCTGTGTGGAAGT
     C W G L L M V L C R T A I S R S I V L E P I Y W N S N S K F L P
               20                       30                       40
201 ACTGTTGGGGACTTTTGTGATGGTTTTGTGCAGAACTGCGATCTCCAGATGTTTAGAGCCTATATCTACTGGAATTCCAACTCCAAATTTCTACC
     G Q G L V L Y P Q I G D K L D I I C P K V D S K T V G Q Y E Y Y K
                       50                       60                       70                       80
301 CGGACACAAGGCCTGTACTATACCCCACAGATAGGAGACAAATTGGATATTATTTGCCCCAAAGTGGACTCTAAAACTGTTGGCCAGTATGAATATTATAAA
     V Y M V D K D Q A D R C T I K K E N T P L L N C A R P D Q D V K F T
                       90                      100                      110
401 GTTTATATGGTTGATAAAGACCAAGCAGACAGATGCACAATTAAGAAGGAGAATACCCCGCTGCTCAACTGTGCCAGAGACCAAGATGTGAAATTCA
     I K F Q E F S P N L W G L E F Q K N K D Y Y I I S T S N G S L E G
                      120                      130                      140
501 CCATCAAGTTTCAAGAATTCAGCCCTAACCTCTGGGGTCTAGAATTTCAGAAGAACAAAGATTACTACATTATATCTACATCAAATGGGTCTTTGGAGGG
     L D N Q E G G V C Q T R A M K I L M K V G Q D A S S A G S A R N H
                      150                      160                      170
601 CCTGGATAACCAGGAGGGAGGGGTGTGCCAGACAAGAGCCATGAAGATCCTCATGAAAGTTGGACAAGATGCAAGTTCTGCTGGATCAGCCAGGAATCAC
     G P T R R P E L E A G T N G R S S T T S P F V K P N P G S S T D G N
                      180                      190                      200                      210
701 GGTCCAACAAGACGTCCAGAGCTCGAAGCTGGTACAAATGGGAGAAGTTCAACAACAAGTCCCTTTGTGAAGCCAAATCCAGGTTCTAGCACCGATGGCA
     S A G H S G N N L L G S E V A L F A G I A S G C I F I V I I I T
                      220                      230                      240
801 ACAGCGCGGGCATTCCGGGAACAATCTCCTGGGTTCCGAAGTGGCCTTATTGCAGGATGCATCAGGATGCATCATCTTCATCGTCATCATCATCAC
```

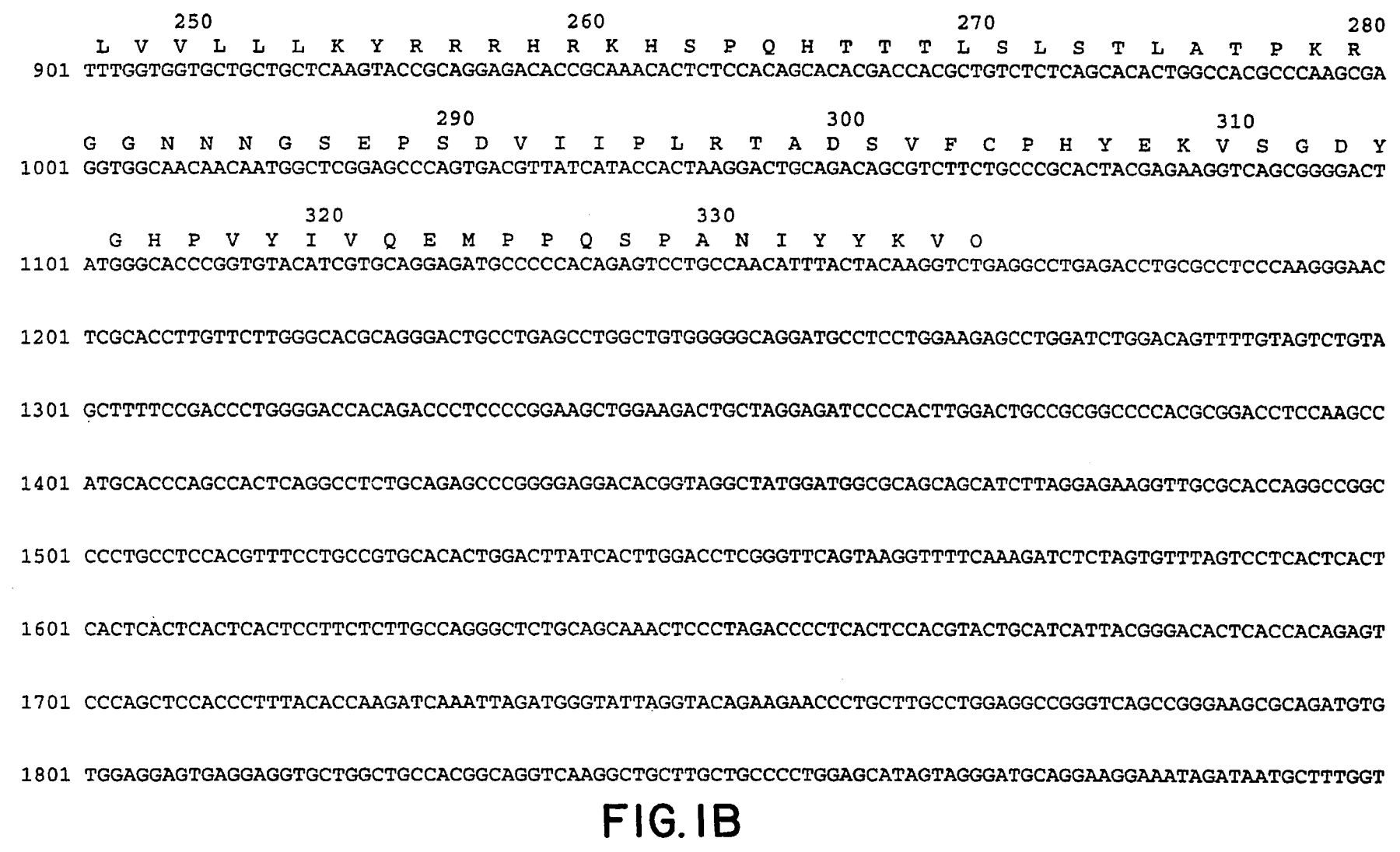

```
1901 TTTTCTGAGAGGACAGAGACAGGTGGGAGGTGACTGACTGGTGAGTGGTGGGGAGCCTTTCACTACCACACAGCTATGCAGCAGGGAATCAAAAGTCCCT
2001 CTCCTGCGGGGAACAAAGGGGCCATTGTTGTGAAAGGACCAGCTAGAGACACAGAGGGAGAGGGCAGGCCTCCGGTGAAGTGCTGGGCAGAACTGCAGAG
2101 GTACTGGAAATAAAAAGCCAGCGCAGAGCTGTGGGAGAGTCCGTCTGCGTCTGCTTTGGAGATGTTTTAAGCAGACTCAGCTGCTATATTACCACGTTTTATT
2201 AAAAACACAGGGAAAGCATTTAGGAGAAGAGCCAAATCTGACCTAGAAGTTGAAAAGCCAAAGTCAAACAGGCTGTAAGTCCATCACCACTG
2301 AGGTTATTGGAGAATTCTCATTAGGAAAGGCAGGTCAGATTCCCCAGGCCCCATAAGTGCCCCTCCCCTGATTGAGCCTTACACGTTGGTTTTT
2401 GGTTTATGGCCGTGCTGTCCGGGCTCCAAGGCAGTACCCGGCTCCATGTCAAAGCAAAGCACACATGCCCACCTCTTAGAGTCCTTGAGATGAAGTA
2501 AGTTATGCCGCGAAGGAGAAAGGCGAAGATAGGAAGATATAAATGAAAGATTTTTACTAATATATATTTT
2601 AAGATTACACACAATACACACCAGAACGTGGAGTTCGGTGGTGGTCGTGGTGGTGATTAAAGTGACCCCAGCGCTTAGTGCTTTAAAAA
2701 GTGAAAGATTGGGTAGCTACTCCCCGAAACGTACCAATAGCAAGAAAAGTATCCATAATGAGAGCAAATGGCAAAATAACACGTCCTGCGGAATCTC
2801 GCAGAACGTAGACTAGGAATGCCAGCCCCCAAATTGATGTGACCCTGCCCCGGGTTAGACAATGATAAAATGCGCTGGCCTTTATTTTCTGTGTTGGG
2901 TTTTCCCTTGCCTTATGGGCTGAAGTGTTCTCTAGAATTTAGCAGGTCACACTGAGGGGATTCCAGTTTAACTGTGGTCCCTCCTCCTCCTACCCCA
3001 TCCCTGCCCTTCCAGAGAATAACAGGAAGCCTTCCTTTTTTTTTTTAAGTGCTATGCAAAAGAGACATCTTTAACAGAGTCCTGTTACTATGGTAA
```

FIG. 1C

```
3101  CATTTGCTTTCTGAATTGGGAGGAAATAAAAATTGTAATGACAGCATTTGAAGGTTCTCAGAGACCTCCAGTGAGTTCTGCAAAAATGAGTTGTCACAGA

3201  GATTATTCCCTACTTCTCAAACCTGAAAATGATGTTGGTTCGATGTGTGTTCGATGTGGGTGTGTGGTACATGTGTGTACATATATGTATAAT

3301  ATATATCTCCAGTATATATATTATATATATCTATATTTCTGTGGAGGGTTGCCATGGCAATCAACTGCAGTACATATGTAGTTCTTTCCATCACCCT

3401  AACCTCTCCTGCGCATTCACACAGAGTTCTTGTAAGCCATCAAAAGTTAATTCTAGGGGAGAGAGGATGAGGCGGGAGACATGGGAAACCGTCTGAT

3501  TTTAATGAAATCAAATGTCTGTGTCATCGGTTGGCTACGTTTTGGTTCTATGCTAAACTGTGAAGAATCGGATGAATTGATGAAGAGTTGAGTTACCTGC

3601  AACCCATTGAGAAGTGTCCTGTGCGTCTGTTTTGTGTCTGGTGCAGAAAATCTACCAACTGTCCCCTTATTGGAGTTGGTTCAGCTTTGGAAA

3701  GTTACTGTAAATGCCTTGCTTGTGTTATTATCATCCCTAGTCACCTGACTTCCGGAGCTTGCACCATCGTGTTTAAGTGAAGACGCTGTAAATAGGTTCAGAT

3801  CTTACCGTCTATGGATTCGGGTGTTACAGTAGCCCTTATTCACCTTTTTAATAAAAATACACATGAAAACGAGACAGTAATGGCTTTTCTTACCCAGATTG

3901  TGTACATAGAGCAATGTTGGTTTTTTATAAAGTCTAAGCAAGATGTTTTGTATAAAATCTGAATTTGCAATGTATTTAGCTACAGCTTTTAACGGCAGT

4001  GTCATCCCCTTTGCACTGTAATGAGGAAAAAAAAGGTATAAAAGGTTGCCGTAATTATGTGCCGTAATTATGTACCATGAATATTTATTT

4101  AATTTCGTTGTCCAATTGTAAGTAACACAGTATTATGCTTGAGTTATAAATATTTTCTTTGTTTTATTTAATAGCCTGTCATAGGTTTTTTTTAA

4201  TCTGCTTTAGTTCCACATGACAGTTAAGCCCACGTTCCACGTCTGTTCAAAATGAATTGTTCTTAAAAATAAA

4301  ATATTTTTTTCCTATGGAAAAAAAAAAAAAGGGGGCCGC
```

```
              300                         310                          320
     I  P  L  R  T  A  D  S  V  F  C  P  H  Y  E  K  V  S  G  D  Y  G  H  P  V  Y  I  V  Q  E  M  P  P
 901 CATCCCGCTAAGGACTGCGGACAGCGTCTTCTGCCCTCACTACGAGAAGGTCAGCGGGGACTACGGGCACCCGGTGTACATCGTCCAGGAGATGCCCCCG
                330
     Q  S  P  A  N  I  Y  Y  K  V  Q
1001 CAGAGCCCCGGCGCGAACATTTACTACAAGGTCTGAGAGGACACCTAAGTGCCCGATGCCTCCCTTGAGGGT

1101 TTGAGAGCCCGCGTGCTGGAGAATTGACTGAAGCACAGCACCGGGGAGAGGGACACTCCTCGGAAGAGCCCCTCGGACTGTGCAGAAGACGCCCATTCGGACTGCTGTGCCGTCCCACGTCTCCT

1201 TTGTAGCATTCGGCCTTGGTGAACACACACGCTCCCTGGAAGCTGTGAAGACAGTGGTTTGTGGACGTTGTGAGCATCCTGGCAGGTGCCCC

1301 CCTCGAAGCCATGTGCTGCGGTCACTCAGGCCTCTGCGGTGCAGAAGGGAAGCAAGGGAAGCCTTGTCACACGGACCTCGGGCTAGTTAAGGTGTGC

1401 AGGATGCCACGCCCTGGAAGGGCCGGCTTCTGCCTGGGGTGCATTTCCCCCGCAGTGCATAACCGACTTGTCACACGGACCTCGGGCTAGTTAAGGTGTGC

1501 AAAGATCTCTAGAGTTTAGTCCTTACTGTCTCCACTCGTTCTGTTACCCAGGGCTCTGCGACCACCTCCACTCTGAGACCTCCACTCCACATCTGCATCACTCA

1601 TGGAACACTCATGTCTGGAGTCCCCTCCAGCCGCTGGCAACACAGCTTCAGTCCATGGGTAATCCGTTCATAGAAATTGTGTTTGCTAACAAGGTG

1701 CCCTTTAGCCAGATGCTAGGCTGTCTGCGAAGAAGGCTAGGAGTTCATAGAAGGGCTGGGAAAGGGCTGGCTGCAATTGCAGCTCACTGCTG

1801 CTGCCCTCTGAAACAGAAAGTTGGAAAGGAAAAAAAGAATTAGTAGCACAGCACTTTGGTTTTGCTGAGATCGAAGAGGCCAGTAGGAGACAC

1901 GACAGCACACAGTGGATTCCAGTGCATGGGGAGGCCGGTCGACGAGCTCGAG
```

```
         1                                                               
muHtkL   1   M A M A R S - R R D S V H K Y C W G L L M V L C R T A I S R S I V L E P I Y W N S S N S K F L P G Q
humHtkL  1   - - M A - - V R R D S V H K Y C W G V L M V L C R T A I S K S I V L E P I Y W N S S N S K F L P G Q
                                                                                                         R N E muHtkL   50  G L V L Y P Q I G D K L D I I C P K V D S K T V G Q - - - Y E Y Y K V Y M V D K D Q A D R C T I K K E
humHtkL  47  G L V L Y P Q I G D K L D I I C P K V D S K T V G Q - - - Y E Y Y K V Y M V D K D Q A D R C T I K K E
                                                                                                         * muHtkL   98  N T P L L N C A R P D Q D - - - - Y K F T I K F Q E F S P N L W G L E F Q K N K D Y Y I I S T S N G S
humHtkL  95  N T P L L N C A K P D Q D - - - - I K F T I K F Q E F S P N L W G L E F Q K N K D Y Y I I S T S N G S muHtkL   145 L E G L D N Q E G G V C Q T R A M K I L M K V G Q D A S S A G S A R - N H G P T R R P E L E A - G T
humHtkL  142 L E G L D N Q E G G V C Q T R A M K I L M K V G Q D A S S A G S T R - N K D P T R R P E L E A - G T muHtkL   193 N G R S S T T S P F V K P N P G S S T D G N S A G H S G N N L L G S E V A L F A G L A S G C L F - G T
humHtkL  190 N G R S S T T S P F V K P N P G S S T D G N S A G H S G N N I L G S E V A L F A G L A S G C L F - G T muHtkL   243 V L T L V L L L K Y R R R H R K H S P Q H T T T L S L S T L A T P K R G G N N N G S E P S D V
humHtkL  240 V L T L V L L L K Y R R R H R K H S P Q H T T T L S L S T L A T P K R T G N N N G S E P S D I muHtkL   293 I I P L R T A D S V F C P H Y E K V S G D Y G H P V Y I V Q E M P P Q S P A N I Y Y K V
humHtkL  290 I I P L R T A D S V F C P H Y E K V S G D Y G H P V Y I V Q E M P P Q S P A N I Y Y K V
```

FIG.4A

```
             380                    390                   400
      P  G  G  D  L  T  F  D  P  G  P  R  D  L  V  E  P  W  V  V  R  G  L  R  P  D  F  T  Y  T  F
1201  CGCCCTGCGGGGGAGACCTGACTTTTGACCCCGGACCCTGGTGTGGTGCGTGGTTCGAGGGCTACGTCCTGAGTTCACCTATACCTT
            410                    420                   430
      E  V  T  A  L  N  G  V  S  S  L  A  T  G  P  V  P  F  E  P  V  N  V  T  T  D  R  E  V  P  P  A  V
1301  TGAGGTCACTGCATTGAACGGGGTCATCCTCCTTAGCCACGGGCCCGTCCCATTTGAGCCTGTCAATGTCACCACTGACCGAGAGTACCTCTGCAGTG
         440                    450                   460                    470
      S  D  I  R  V  T  R  S  S  P  S  S  L  A  W  A  V  P  R  A  P  S  G  A  V  L  D  Y  E  V  K  Y
1401  TCTGACATCCGGGTGACGCGGTCCTCACCCAGCAGCTTGAGCCTGGCCTGGGCTGTTCCCCGGGCTCCCAGTGGGGCTGTGCTGGACTACGAGGTCAAAT
                        480                    490                   500
      H  E  K  G  A  E  G  P  S  S  V  R  F  L  K  T  S  E  N  R  A  E  L  R  G  L  K  R  G  A  S  Y  L
1501  ACCATGAGAAGGGCGCCGAGGGTCCCAGCAGCGTGCGGTTCCTGAAGACGTCAGAGAACCGGGCAGAGCTGCGGGGGCTGAAGCGGGGAGCCAGCTACCT
                510                    520                   530
      V  Q  V  R  A  R  S  E  A  G  Y  G  P  F  G  Q  E  H  H  S  Q  T  Q  L  D  E  S  E  G  W  R  E  Q
1601  GGTGCAGGTACGGGCCCGCTCTGAGGCCGGCTACGGGCCCTTCGGCCAGGAACATCACAGCCAGACCCAACTGGATGAGAGCGAGGGCTGGCGGGAGCAG
                       540                    550                   560                    570
      L  A  L  I  A  G  T  A  V  V  G  V  V  L  V  V  I  V  V  A  V  L  C  L  R  K  Q  S  N  G  R  E
1701  CTGGCCCTGATTGCGGGCACCGCAGTCGTGGGGGTGGTCCTCGTGGTCATTGTGGTCGCAGTTCTCTGCCTCAGGAAGCAGAGCAATGGGAGAGAG
                580                    590                   600
      A  E  Y  S  D  K  H  G  Q  Y  L  I  G  H  G  T  K  V  Y  I  D  P  F  T  Y  E  D  P  N  E  A  V  R
1801  AAGCAGAATATTCGGACACAAACACGGACAGTATCTCAGGACATGGTCTACAATCGGACACCCCTTCACTTACTATGAAGACCCTAATGAGGCTGTGAG
                    610                    620                   630
      E  F  A  K  E  I  D  V  S  Y  V  K  I  E  E  V  I  G  A  G  E  F  G  E  V  C  R  G  R  L  K  A  P
1901  GGAATTTGCAAAAGAGATCGATGTCTCCTACGTCAAGATTGAAGAGGTGATTGGTGCAGGTGAGTTTGGCGAGGTGTGCCGGGGACGTCTCAAGGCCCA
                640                    650                   660                    670
      G  K  K  E  S  C  V  A  I  K  T  L  K  G  G  Y  T  E  R  Q  R  R  E  F  L  S  E  A  S  I  M  G  Q
2001  GGGAAGAAGGAGAGCTGTGTGGCAATCAAGACCCTGAAGGGTGGCTACACCGAGCGGCAGCGCCGTGAGTTTCTGAGCGAGGCCTCCATCATGGGCCAGT
                       680                    690                   700
      F  E  H  P  N  I  I  R  L  E  G  V  V  T  N  S  M  P  V  M  I  L  T  E  F  M  E  N  G  A  L  D  S  F
2101  TCGAGCACCCCAATATCATCCGCCTGGAGGGTGTTGTCACCAACAGCATGCCCGTCATGATTCTCACAGAGTTCATGGAGAACGGGGCCCTGGACTCCTT
               710                    720                   730
      L  R  L  N  D  G  Q  F  T  V  I  Q  L  V  G  M  L  R  G  I  A  S  G  M  R  Y  L  A  E  M  S  Y  V
2201  CCTGCGCCTAAACGACGGACAGTTCACAGTCATCCAGCTCGTGGGCATGCTGCGGGGCATCGCCTCGGGCATGCGCTACCTTGCCGAGATGAGCTACGTC
                    740                    750                   760                    770
      H  R  D  L  A  A  R  N  I  L  V  N  S  N  L  V  C  K  V  S  D  F  G  L  S  R  F  L  E  E  N  S  S  D
2301  CACCGAGACCTGGCTGCTCGCAACATCCTAGTCAACATCAACCTCGTCTGCAAAGTGTCTGACTTTGGCCTTTCCCGATTCCTGGAGGAGAACTCTTCCG
```

METHOD FOR USING HTK LIGAND

CROSS REFERENCES

This application is a divisional of co-pending U.S. application Ser. No. 08/277,722 filed 20 Jul. 1994, which application is incorporated herein by reference and to which application priority is claimed under 35 USC 120.

BACKGROUND OF THE INVENTION

1. Field of the Invention

The present invention pertains generally to a receptor protein tyrosine kinase (rPTK) ligand. More particularly, the invention relates to a novel ligand which binds to, and activates, the hepatoma transmembrane kinase (Htk) receptor (also known as HpTK 5 receptor) and the isolation and recombinant production of the same.

2. Description of Related Art

Transduction of signals that regulate cell growth and differentiation is regulated in part by phosphorylation of various cellular proteins. Protein tyrosine kinases are enzymes that catalyze this process. Members of the protein tyrosine kinase family can be recognized by the presence of several conserved amino acid regions in the tyrosine kinase catalytic domain (Hanks et al., *Science* 241:42–52 [1988]). The tyrosine kinase domain is involved in the signal transduction pathways of mitogenesis, transformation and cell differentiation. Certain tyrosine kinases predominantly stimulate cell growth and differentiation, whereas other tyrosine kinases arrest growth and promote differentiation. Furthermore, depending on the cellular environment in which it is expressed, the same tyrosine kinase may either stimulate, or inhibit, cell proliferation. See Schlessinger et al., *Neuron* 9:383–391 [1992].

Receptor protein tyrosine kinases (rPTKs) convey extracellular signals to intracellular signaling pathways thereby controlling cell proliferation and differentiation. These rPTKs share a similar architecture, with an intracellular catalytic portion, a transmembrane domain and an extracellular ligand-binding domain. (Schlessinger et al., supra). The extracellular domains (ECDs), which are responsible for ligand binding and transmission of biological signals, have been shown to be composed of a number of distinct structural motifs. The intracellular domain comprises a catalytic protein tyrosine kinase.

Receptor tyrosine kinases are categorized in several classes, according to sequence and structural similarities. For example, Class V receptors have cysteine rich and fibronectin Type III regions in the extracellular domain and include the EPH, ELK, ERK, EEK, ECK and HEK receptors. For a review of the various classes of receptor tyrosine kinases and their functions, see, e.g., Hanks et al., supra and Schlessinger et al., supra.

Protein ligands for receptor protein tyrosine kinases bind to the extracellular domain of their cognate receptors at the cell surface and thereby stimulate tyrosine phosphorylation. Several of these ligands are growth factors or cytokines, such as insulin-like growth factor 1 (IGF-1), epidermal growth factor (EGF), fibroblast growth factor (FGF), and nerve growth factor (NGF). Ligands for a number of tyrosine kinase receptors have been shown to function within the hematopoietic system. For example, the ligand for murine flt3/flk-2 tyrosine kinase receptor, recently cloned, stimulates the proliferation of primitive mouse hematopoietic cells and human CD34-positive bone marrow cells. Lyman et al., *Cell* 75:1157–1167 (1993).

A protein ligand which stimulates phosphorylation of the ECK receptor has recently been cloned and expressed in CHO cells. Bartley et al., *Nature* 368:558–560 (1994). This ECK ligand was found to be identical to B61, a molecule previously isolated by Holzman et al., *Mol. Cell. Biol.* 10:5830–5838 (1990).

A receptor tyrosine kinase has been recently identified and cloned from a human hepatocellular carcinoma cell line, Hep 3B. This receptor, called "Htk" receptor or "HpTK 5" receptor, is thought to belong to the Class V or EPH subfamily or rPTKs. See Bennett et al., *J. Biol. Chem.*, 269(19):14211–14218 (1994).

Northern blot analysis of human fetal tissues revealed that expression of Htk receptor nucleic acid occurs in heart, lung, liver, brain and kidney. In adult human tissue, no signal was detectable in brain, while placenta had a particularly intense signal followed by kidney, liver, lung and pancreas. Skeletal muscle and heart were of lower signal intensity. See Bennett et al., supra.

Htk receptor nucleic acid expression in human tumor cell lines has also been analyzed by Northern blot analysis. Cell lines derived from liver, breast (MCF-7), colon (Colo 205), lung (NCI 69), melanocyte (HM-1) and cervix (HeLa) had detectable signals of appropriate size. Message was present in select cell lines of hematopoietic origin. K562 (a primitive myeloid cell with multipotential), THP-1 (a monocytoid cell), U937 (a myelomonocytic cell line), Hep3B (a human hepatocarcinoma cell line), and CMK (of megakaryocytic origin) were all positive for Htk receptor message, but lymphoid (H9, Jurkat, JH-1, Raji, Ramos) or select other myeloid cells (KG-1 or KMT2) had no detectable transcript by Northern analysis. See Bennett et al., supra.

The mouse homologue to the Htk receptor, called "myk-1", was isolated from mammary gland epithelia. See Andres et al., *Oncogene* 9:1461–1467 (1994). Andres et al. report that myk-1 is induced during proliferation of mammary epithelium and down-regulated during its differentiation. Additionally, deregulated expression of the receptor is considered to potentially represent an early event in mammary gland carcinogenesis (see Andres et al., supra).

However, it is believed that the protein ligand for the Htk receptor has not been heretofore disclosed. Therefore, it is an object of the invention to provide a ligand to the Htk receptor.

It is a further object of the invention to provide nucleic acid encoding the Htk ligand so that the ligand can be made by recombinant DNA techniques.

These and other objects will be apparent to the ordinary artisan upon consideration of the specification as a whole.

SUMMARY OF THE INVENTION

These objects are accomplished, in one aspect, by providing isolated Htk ligand that may be antigenically or biologically active. In one embodiment, the invention provides a soluble form of the ligand with at least the transmembrane region deleted. Usually, the cytoplasmic domain will also be absent.

One example of a soluble form of the Htk ligand is an immunoadhesin which is a fusion of the extracellular domain of the Htk ligand and an immunoglobulin sequence.

The invention also pertains to other chimeras comprising the Htk ligand (or a portion thereof) fused to another polypeptide. An example of such a chimera is epitope tagged Htk ligand.

In another aspect, the invention provides a composition comprising biologically active Htk ligand and a pharmaceutically acceptable carrier. Preferably, the Htk ligand is present in a soluble form in the pharmaceutical composition.

The invention also provides isolated nucleic acid sequences encoding Htk ligand and Htk ligand chimeras.

The nucleic acid can be provided in a replicable vector which may be transformed into a host cell in one embodiment of the invention. A method of using the nucleic acid encoding the Htk ligand to effect the production of the novel protein is also provided which comprises expressing the nucleic acid in a culture of the transformed host cells and recovering the protein from the host cell culture.

The invention also provides a method which involves contacting the Htk receptor with the Htk ligand in order to cause phosphorylation of the kinase domain thereof.

The invention also provides a monoclonal antibody which binds to the Htk ligand, which can be used to detect the presence of the Htk ligand in a biological sample suspected of having the ligand, for example.

BRIEF DESCRIPTION OF THE DRAWINGS

FIGS. 1A–1B depict an alignment of the nucleotide sequence (SEQ ID NO: 1) and deduced amino acid sequence (SEQ ID NO: 2) of the murine Htk ligand described herein.

FIG. 2 depicts an alignment of the nucleotide (SEQ ID NO: 3) and deduced amino acid sequence (SEQ ID NO: 4) of the human Htk ligand described herein.

FIG. 3 shows an alignment of the amino acid sequences of murine Htk ligand (muHtkL) and human Htk ligand (humHtkL) (SEQ ID NOS: 2 and 4, respectively). Identical residues are enclosed within line boundaries. The shaded area represents a transmembrane domain. The extracellular domain and intracellular domain are N-terminal and C-terminal to the transmembrane domain, respectively. The amino acid predicted to be the cleavage site for the signal peptide is indicated by an arrow. The potential N-linked glycosylation sites are marked with an (*) and conserved cysteines are marked with an (▼).

FIG. 4 depicts the nucleotide sequence (SEQ ID NO: 5) and deduced amino acid sequence (SEQ ID NO: 6) of the human Htk receptor disclosed in Bennett et al., supra. The amino acid predicted to be the cleavage site for the signal peptide is indicated by an arrow. Cysteine residues conserved among ELK subfamily members are circled and the transmembrane region is overlined.

DETAILED DESCRIPTION OF THE PREFERRED EMBODIMENTS

I. Definitions

Figure 5A:
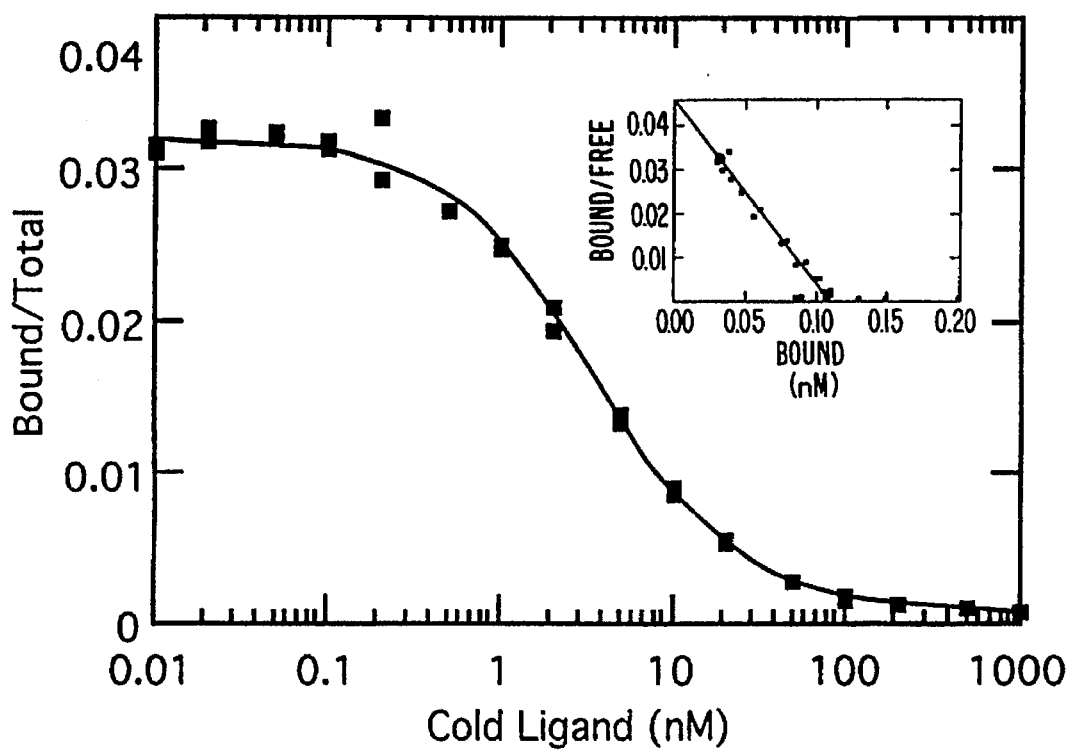
FIGS. 5A–5B show binding competition curves of Htk-Fc to the SV40MES 13 cell line (FIG. 5A) or to recombinant murine Htk ligand expressed in COS-7 cells (FIG. 5B). Scatchard representation of each binding curve is shown in the inset and revealed K's of 3 nM and 0.5 nM, respectively.

In describing the present invention, the following terms will be employed, and are intended to be defined as indicated below.

"Htk ligand" is defined herein to be any polypeptide sequence that binds to and activates a rPTK, preferably binds to the extracellular domain of the Htk receptor and thereby activates the intracellular tyrosine kinase domain thereof. Activation of the rPTK can be measured by autophosphorylation of tyrosine residues in the intracellular domain of the rPTK. See Example 4 herein for an exemplary technique for measuring receptor autophosphorylation. The Htk ligand may also possess another biological property of a naturally occurring polypeptide, which polypeptide has either of the amino acid sequences shown in FIG. 3.

Figure 4A:
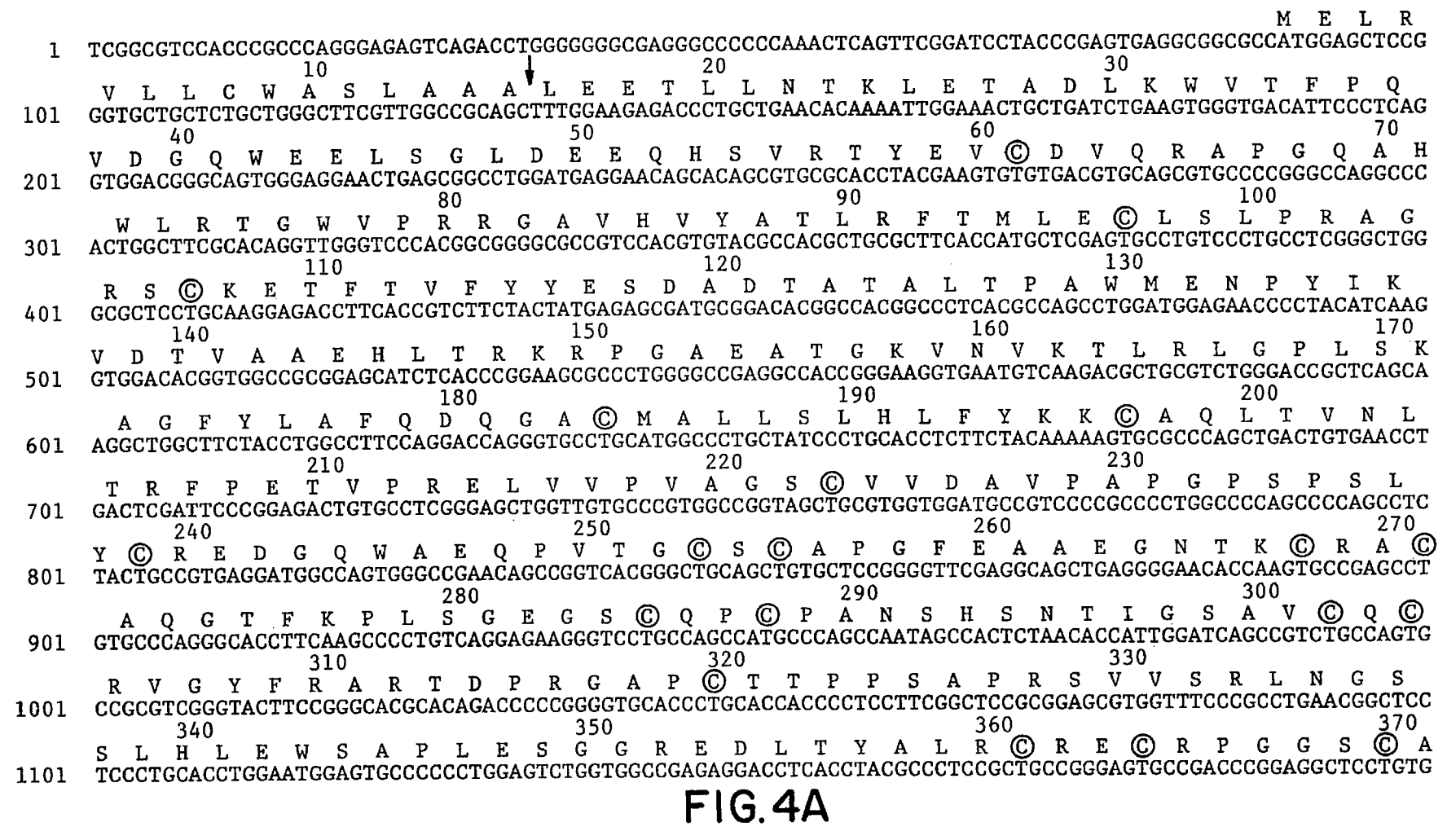
Figure 4C:
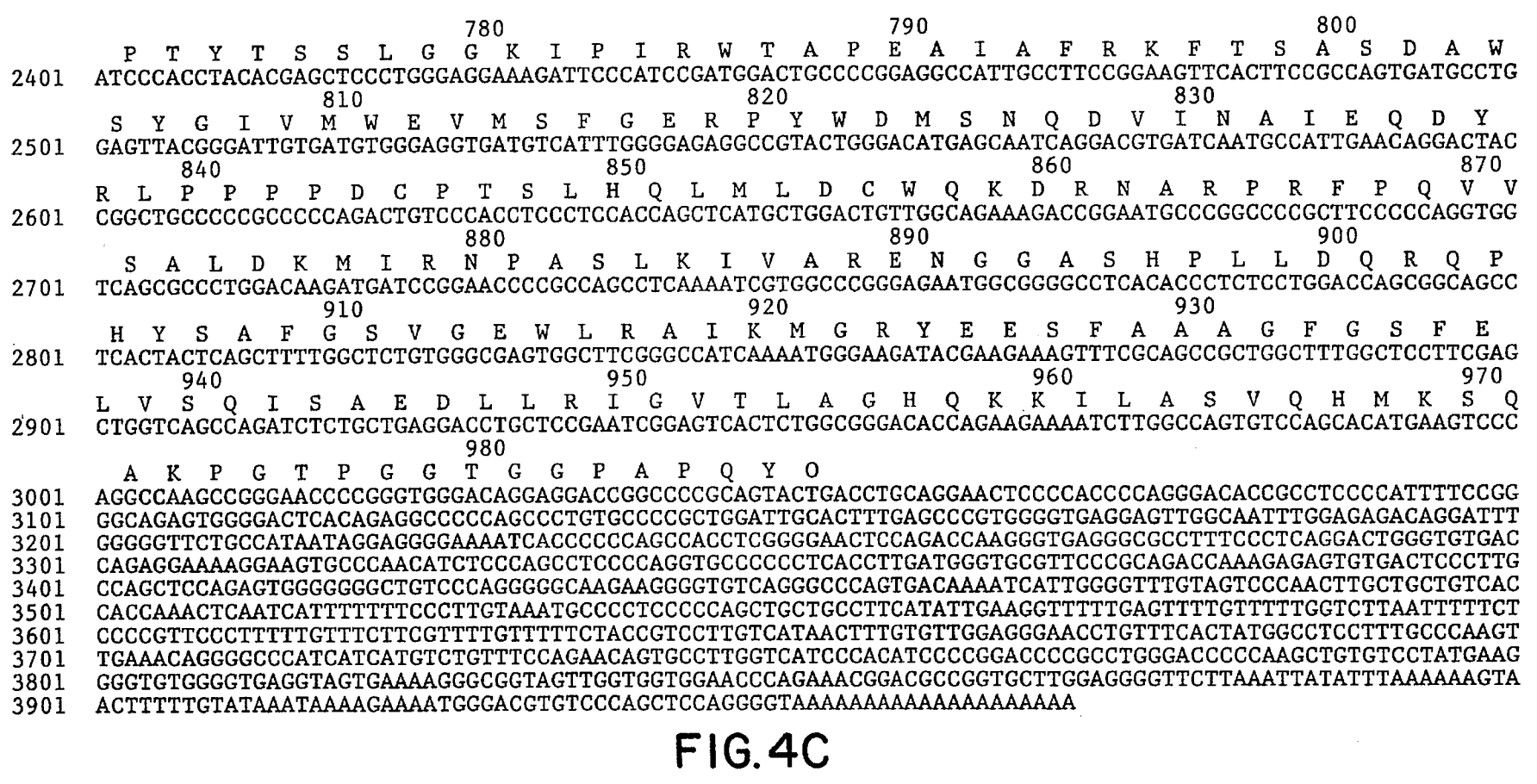

"Biological property" for the purposes herein means an in vivo effector or antigenic function or activity that is directly or indirectly performed by the Htk ligand as shown by the sequences in FIG. 3 (whether in its native or denatured conformation). A principal effector function is the ability of the Htk ligand to bind to, and activate, a rPTK such as the Htk receptor (also known as the HpTK 5 receptor), which is disclosed in Bennett et al., supra. The Htk receptor is a rPTK of the Class V or EPH subfamily of rPTKs. The nucleotide and amino acid sequence of the Htk receptor are depicted in FIG. 4. Generally, the ligand will bind to the extracellular domain of the Htk receptor and thereby activate the intracellular tyrosine kinase domain thereof. Consequently, binding of the ligand to the receptor may result in enhancement or inhibition of proliferation and/or differentiation and/or activation of cells having a receptor for the Htk ligand in vivo or in vitro. Binding of the ligand to the Htk receptor can be determined using conventional techniques, including competitive binding methods, such as RIAs, ELISAs, and other competitive binding assays. Ligand/receptor complexes can be identified using such separation methods as filtration, centrifugation, flow cytometry (see, e.g., Lyman et al., Cell 75:1157–1167 [1993]; Urdal et al., J. Biol. Chem. 263:2870–2877 [1988]; and Gearing et al., EMBO J 8:3667–3676 [1989]), and the like. Results from binding studies can be analyzed using any conventional graphical representation of the binding data, such as Scatchard analysis (Scatchard, Ann. NY Acad. Sci. 51:660–672 [1949]; and Goodwin et al., Cell 73:447–456[1993]), and the like. Since the Htk ligand induces phosphorylation of the Htk receptor, conventional tyrosine phosphorylation assays, such as the assay described in Example 4 herein, can also be used as an indication of the formation of an Htk receptor/ligand complex. Other effector functions include signal transduction, any enzyme activity or enzyme modulatory activity (e.g., tyrosine kinase activity), or any structural role, for example. However, effector functions do not include possession of an epitope or antigenic site that is capable of cross-reacting with antibodies raised against Htk ligand. An antigenic function means possession of an epitope or antigenic site that is capable of cross-reacting with antibodies raised against the polypeptide sequence of a naturally occurring polypeptide comprising either of the polypeptide sequences of FIG. 3.

"Biologically active" Htk ligand is defined herein as a polypeptide that shares an effector function of Htk ligand and that may (but need not) in addition possess an antigenic function. A principal known effector function of Htk ligand is its ability to cause protein phosphorylation of the Htk receptor.

"Antigenically active" Htk ligand is defined as a polypeptide that possesses an antigenic function of Htk ligand and that may (but need not) in addition possess an effector function.

In preferred embodiments, antigenically active Htk ligand is a polypeptide that binds with an affinity of at least about $10^6$ l/mole to an antibody capable of binding Htk ligand. Ordinarily, the polypeptide binds with an affinity of at least about $10^7$ l/mole. Isolated antibody capable of binding Htk ligand is an antibody that is identified and separated from a component of the natural environment in which it may be present. Most preferably, the antigenically active Htk ligand is a polypeptide that binds to an antibody capable of binding Htk ligand in its native conformation. Htk ligand in its native conformation is Htk ligand as found in nature that has not been denatured by chaotropic agents, heat, or other treatment that substantially modifies the three-dimensional structure of Htk ligand as determined, for example, by migration on non-reducing, non-denaturing sizing gels.

Ordinarily, biologically or antigenically active Htk ligand will have an amino acid sequence having at least 75% amino acid sequence identity with either of the mature Htk ligand amino acid sequences shown in FIG. 3, more preferably at least 80%, more preferably at least 85%, more preferably at least 90%, and most preferably at least 95%. Identity or homology with respect to this sequence is defined herein as the percentage of amino acid residues in the candidate sequence that are identical with the Htk ligand residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the Htk ligand sequence shall be construed as affecting sequence identity or homology.

Thus, the biologically active and antigenically active Htk ligand polypeptides that are the subject of this invention include the polypeptide represented by the entire translated nucleotide sequence of Htk ligand (including the signal sequence thereof); mature Htk ligand with the signal sequence cleaved therefrom; fragments consisting essentially of the intracellular domain or transmembrane domain of the Htk ligand; fragments of the Htk ligand having a consecutive sequence of at least 5, 10, 15, 20, 25, 30, or 40 amino acid residues from Htk ligand; amino acid sequence variants of Htk ligand wherein an amino acid residue has been inserted N- or C-terminal to, or within, Htk ligand or its fragment as defined above; amino acid sequence variants of Htk ligand or its fragment as defined above wherein an amino acid residue of Htk ligand or its fragment as defined above has been substituted by another residue, including predetermined mutations by, e.g., site-directed or PCR mutagenesis. Htk ligand of various animal species such as rabbit, rat, porcine, non-human primate, equine, murine, and ovine Htk ligand and alleles or other naturally occurring variants of the foregoing and human Htk ligand; derivatives of Htk ligand or its fragments as defined above wherein Htk ligand or its fragments have been covalent modified, by substitution, chemical, enzymatic, or other appropriate means, with a moiety other than a naturally occurring amino acid; and glycosylation variants of Htk ligand (insertion of a glycosylation site or alteration of any glycosylation site by deletion, insertion, or substitution of suitable residues). The preferred Htk ligand is human Htk ligand, especially native human Htk ligand having the sequence shown in FIG. 2.

In one preferred embodiment, the Htk ligand comprises soluble Htk ligand. By "soluble Htk ligand" is meant Htk ligand which is essentially free of at least the transmembrane and, optionally, the intracellular domain of native Htk ligand. By "essentially free" is meant that the soluble Htk ligand sequence has less than 2% of the transmembrane domain, preferably 1.0–0% of the transmembrane domain, and more preferably 0.5–0% of this domain. The transmembrane domains of the native murine and human amino acid sequences are delineated in FIG. 30 i.e., resides 228 to 253 for murine Htk ligand and residues 225 to 250 for human Htk ligand. Such soluble Htk ligands may have advantages from a therapeutic standpoint because they are generally soluble in the patient's blood stream, for example. Similarly, such soluble ligands may prove to be particularly useful as diagnostics since they are expected to have a reduced tendency to incorporate in the cell membrane.

One example of a soluble form of the Htk ligand is an "immunoadhesin". The term "immunoadhesin" is used interchangeably with the expression "Htk ligand-immunoglobulin chimera" and refers to a chimeric molecule that combines the extracellular domain (ECD) of the Htk ligand with an immunoglobulin sequence. The immunoglobulin sequence preferably, but not necessarily, is an immunoglobulin constant domain. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3.

The expression "extracellular domain" or "ECD" when used herein refers to any polypeptide sequence that shares a receptor binding function of the extracellular domain of the naturally occurring Htk ligand disclosed herein. Receptor binding function refers to the ability of the polypeptide to bind the extracellular domain of a rPTK, such as the Htk receptor, and, optionally, activate the receptor. Accordingly, it is not necessary to include the entire extracellular domain since smaller segments are commonly found to be adequate for receptor binding. The term ECD encompasses polypeptide sequences in which the cytoplasmic domain and hydrophobic transmembrane sequence (and, optionally, 1–20 amino acids amino-terminal to the transmembrane domain) of the mature Htk ligand have been deleted. The extracellular domain of the Htk ligand is delineated in FIG. 3 (i.e., it is amino-terminal to the transmembrane domain).

The term "epitope tagged" when used herein refers to a chimeric polypeptide comprising the entire Htk ligand, or a portion thereof, fused to a "tag polypeptide". The tag polypeptide has enough residues to provide an epitope against which an antibody thereagainst can be made, yet is short enough such that it does not interfere with activity of the Htk ligand. The tag polypeptide preferably also is fairly unique so that the antibody thereagainst does not substantially cross-react with other epitopes. Suitable tag polypeptides generally have at least 6 amino acid residues and usually between about 8–50 amino acid residues (preferably between about 9–30 residues).

An "exogenous" therapeutic compound is defined herein to mean a therapeutic compound that is foreign to the mammalian patient, or homologous to a compound found in the mammalian patient but produced outside the mammalian patient.

"Isolated", when used to describe the various proteins disclosed herein, means protein that has been identified and separated and/or recovered from a component of its natural environment. Contaminant components of its natural environment are materials that would interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the Htk ligand natural environment will not be present. Ordinarily, however, isolated protein will be prepared by at least one purification step.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

Figure 2A:
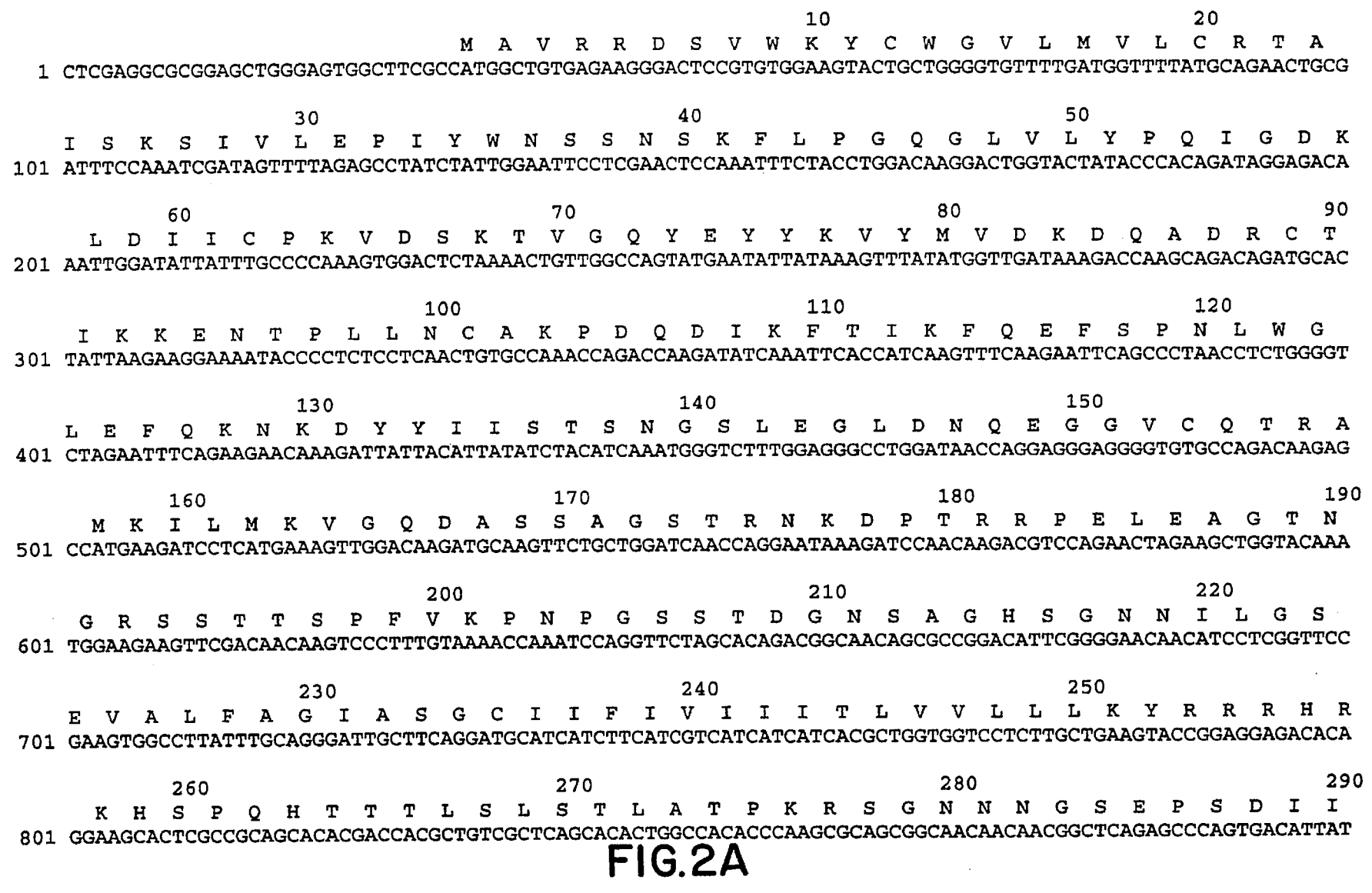

In accordance with this invention, "Htk ligand nucleic acid" or a "Htk ligand nucleic acid molecule" is RNA or DNA containing greater than ten bases that encodes a biologically active or antigenically active Htk ligand, is complementary to nucleic acid sequence encoding such Htk ligand, or hybridizes to nucleic acid sequence encoding such Htk ligand and remains stably bound to it under stringent conditions. The nucleic acid optionally includes the regions of the nucleic acid sequences of FIG. 1A and FIG. 2 which encode the signal sequences. In one embodiment, the nucleic acid sequence is selected from:

(a) the coding regions of the nucleic acid sequences of FIG. 1A or FIG. 2;

(b) a sequence corresponding to either of the sequences of (a) within the scope of degeneracy of the genetic code; or (c) a sequence which hybridizes with a sequence complementary to the sequences of (a) or (b) under stringent conditions and which codes for a biologically active Htk ligand.

In one preferred embodiment, the nucleic acid encodes soluble Htk ligand wherein the nucleic acid encoding the transmembrane region, and optionally the cytoplasmic region, of the polypeptide has been deleted.

Preferably, the Htk ligand nucleic acid molecule encodes a polypeptide sharing at least 75% sequence identity, more preferably at least 80%, still more preferably at least 85%, even more preferably at least 90%, and most preferably 95%, with either of the Htk ligand amino acid sequences shown in FIG. 3. Preferably, the Htk ligand nucleic acid molecule that hybridizes to nucleic acid sequence encoding Htk ligand contains at least 20, more preferably 40, and most preferably 90 bases.

"Stringent conditions" are those that (1) employ low ionic strength and high temperature for washing, for example, 0.015M NaCl/0.0015M sodium citrate/0.1% NaDodSO$_4$ at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl 75 mM sodium citrate at 42° C.; or (3) employ 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

An "isolated" Htk ligand nucleic acid molecule is a nucleic acid molecule that is identified and, separated from at least one contaminant nucleic acid molecule with which it is ordinarily associated in the natural source of the Htk ligand nucleic acid. An isolated Htk ligand nucleic acid molecule is other than in the form or setting in which it is found in nature. Isolated Htk ligand nucleic acid molecules therefore are distinguished from the Htk ligand nucleic acid molecule as it exists in natural cells. However, an isolated Htk ligand nucleic acid molecule includes Htk ligand nucleic acid molecules contained in cells that ordinarily express Htk ligand where, for example, the nucleic acid molecule is in a chromosomal location different from that of natural cells.

The isolated Htk ligand polypeptide, Htk ligand nucleic acid, or Htk ligand antibody may be labeled for diagnostic and probe purposes, using a label as described and defined further below in the discussion on uses of Htk ligand antibodies.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The term "antibody" is used in the broadest sense and specifically covers single anti-Htk ligand monoclonal antibodies (including agonist and antagonist antibodies) and anti-Htk ligand antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-Htk ligand antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. U.S. Pat. No. 4,816,567 and Mage & Lamoyi, in *Monoclonal Antibody Production Techniques and Applications*, pp.79–97 (Marcel Dekker, Inc., New York (1987)].

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 255:495 (1975), or may be made by recombinant DNA methods (U.S. Pat. No. 4,816,567). The "monoclonal antibodies" may also be isolated from phage libraries generated using the techniques described in McCafferty et al., *Nature* 348:552–554 (1990), for example.

"Humanized" forms of non-human (e.g. murine) antibodies are specific chimeric immunoglobulins, immunoglobulin chains or fragments thereof (such as Fv, Fab, Fab', F(ab') or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

II. Modes for Practicing Out the Invention

The present invention is based on the discovery of a novel Htk ligand which binds to, and activates, the Htk receptor.

The murine Htk ligand cDNA sequence is depicted in FIGS. 1A–B. The predicted molecular weight of the protein following signal peptide cleavage is 34 kD with an estimated pI of 8.9. Similarly, the human Htk ligand has been identified and isolated. The nucleotide and amino acid sequences of the human Htk ligand are shown in FIG. 2. The murine and human ligands show 96% homology at the amino acid level, demonstrating a high degree of conservation between species. A description follows as to the preparation of Htk ligand and variants thereof.

1. Preparation of Natural Sequence Htk Ligand and Variants Thereof

Most of the discussion below pertains to production of Htk ligand by culturing cells transformed with a vector containing Htk ligand nucleic acid and recovering the polypeptide from the cell culture. It is further envisioned that the Htk ligand of this invention may be produced by homologous recombination, as provided for in WO 91/06667, published 16 May 1991.

Briefly, this method involves transforming primary mammalian cells containing endogenous Htk ligand gene (e.g., human cells if the desired Htk ligand is human) with a construct (i.e., vector) comprising an amplifiable gene [such as dihydrofolate reductase (DHFR) or others discussed below] and at least one flanking region of a length of at least about 150 bp that is homologous with a DNA sequence at the locus of the coding region of the Htk ligand gene to provide amplification of the Htk ligand gene. The amplifiable gene must be at a site that does not interfere with expression of the Htk ligand gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing Htk ligand are grown so as to express the gene and produce the protein.

A. Isolation of DNA Encoding Htk Ligand

The DNA encoding Htk ligand may be obtained from any cDNA library prepared from tissue believed to possess the Htk ligand mRNA and to express it at a detectable level. Accordingly, human Htk ligand DNA can be conveniently obtained from a cDNA library prepared from human fetal lung or brain tissue. The murine Htk ligand DNA can be derived from a cDNA library of the SV40MES 13 cell line, for example. The Htk ligand gene may also be obtained from a genomic library or by oligonucleotide synthesis.

Libraries are screened with probes (such as antibodies to the Htk ligand or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the gene encoding Htk ligand is to use PCR methodology as described in section 14 of Sambrook et al., supra.

A preferred method of practicing this invention is to use carefully selected oligonucleotide sequences to screen cDNA libraries from various tissues, preferably mammalian fetal lung or brain lines, more preferably, human fetal lung or brain cell lines. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$p-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the Htk ligand nucleic acid that encodes a full-length polypeptide. In some preferred embodiments, the nucleic acid sequence includes the native Htk ligand signal sequence. Nucleic acid having all the protein coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of Native Htk Ligand

Amino acid sequence variants of Htk ligand are prepared by introducing appropriate nucleotide changes into the Htk ligand DNA, or by synthesis of the desired Htk ligand polypeptide. Such variants include, for example, deletions from, or insertions or substitutions of, residues within the amino acid sequences shown for the Htk ligands in FIG. 3. Any combination of deletion, insertion, and substitution is made to arrive at the final construct, provided that the final construct possesses the desired characteristics. The amino acid changes also may alter post-translational processes of the Htk ligand, such as changing the number or position of glycosylation sites, altering the membrane anchoring characteristics, and/or altering the intracellular location of the Htk ligand by inserting, deleting, or otherwise affecting the leader sequence of the Htk ligand.

For the design of amino acid sequence variants of Htk ligand, the location of the mutation site and the nature of the mutation will depend on the Htk ligand characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the Htk ligand polypeptide that are preferred locations for mutagenesis is called "alanine scanning mutagenesis," as described by Cunningham and Wells, *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed Htk ligand variants are screened for the optimal combination of desired activity.

There are two principal variables in the construction of amino acid sequence variants: the location of the mutation site and the nature of the mutation. These are variants of the sequences of FIG. 3, and may represent naturally occurring alleles (which will not require manipulation of the Htk ligand DNA) or predetermined mutant forms made by mutating the DNA, either to arrive at an allele or a variant not found in nature. In general, the location and nature of the mutation chosen will depend upon the Htk ligand characteristic to be modified. Obviously, such variations that, for example, convert Htk ligand into a known receptor protein tyrosine kinase ligand are not included within the scope of this invention.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among Htk ligand and known Htk ligands (which share the most sequence identity to the human Htk ligand amino acid sequence) to modify the activity of Htk ligand. Deletions from Htk ligand in areas of substantial homology with homologous Htk ligand proteins will be more likely to modify the biological activity of Htk ligand more significantly. The number of consecutive deletions will be selected so as to preserve the tertiary structure of Htk ligand in the affected domain, e.g., beta-pleated sheet or alpha helix.

One preferred deletional variant is the soluble Htk ligand defined herein. This variant of the Htk ligand has the transmembrane and, optionally, intracellular domains deleted using the techniques for generating deletional variants.

Amino acid sequence insertions include amino- and/or carboxylterminal fusions ranging in length from one residue to polypeptides containing a hundred or more residues, as well as intrasequence insertions of single or multiple amino acid residues. Intrasequence insertions (i.e., insertions within the mature Htk ligand sequence) may range generally from about 1 to 10 residues, more preferably 1 to 5, most preferably 1 to 3. Insertions are preferably made in even numbers of residues, but this is not required. Examples of terminal insertions include mature Htk ligand with an N-terminal methionyl residue, an artifact of the direct expression of mature Htk ligand in recombinant cell culture, and fusion of a heterologous N-terminal signal sequence to the N-terminus of the mature Htk ligand molecule to facilitate the secretion of mature Htk ligand from recombinant hosts. Such signal sequences generally will be obtained from, and thus homologous to, the intended host cell species. Suitable sequences include STII or lpp for *E. coli*, alpha factor or invertase for yeast, and viral signals such as herpes gD for mammalian cells.

Other insertional variants of the Htk ligand molecule include the fusion to the N- or C-terminus of Htk ligand of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 Apr. 1989.

A third group of variants are amino acid substitution variants. These variants have at least one amino acid residue in the Htk ligand molecule removed and a different residue inserted in its place. The sites of greatest interest for substitutional mutagenesis include sites identified as the active site(s) of Htk ligand and sites where the amino acids found in the known analogues are substantially different in terms of side-chain bulk, charge, or hydrophobicity, but where there is also a high degree of sequence identity at the selected site within various animal Htk ligand species. Other sites of interest are those in which particular residues of the Htk ligand obtained from various species are identical. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |

TABLE 1-continued

| Original Residue | Exemplary Substitutions | Preferred Substitutions |
|---|---|---|
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the Htk ligand are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: ash, gln, his, lys, arg;

(5) residues that influence chain orientation: gly, pro; and (6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more internal protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of Htk ligand also may be substituted, generally with serine, to improve the oxidative stability of the molecule and prevent aberrant crosslinking.

Nucleic acid molecules encoding amino acid sequence variants of Htk ligand are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of Htk ligand.

Oligonucleotide-mediated mutagenesis is a preferred method for preparing substitution, deletion, and insertion variants of Htk ligand DNA. This technique is well known in the art as described by Adelman et al., *DNA,* 2:183 (1983). Briefly, Htk ligand DNA is altered by hybridizing an oligonucleotide encoding the desired mutation to a DNA template, where the template is the single-stranded form of a plasmid or bacteriophage containing the unaltered or native DNA sequence of Htk ligand. After hybridization, a DNA polymerase is used to synthesize an entire second complementary strand of the template that will thus incorporate the oligonucleotide primer, and will code for the selected alteration in the Htk ligand DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA* 75:5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.* 153:3 (1987). Thus, the DNA that is to be mutated may be inserted into one of these vectors to generate single-stranded template. Production of the single-stranded template is described in Sections 4.21–4.41 of Sambrook et al., supra.

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of Htk ligand, and the other strand (the original template) encodes the native, unaltered sequence of Htk ligand. This heteroduplex molecule is then transformed into a suitable host cell, usually a prokaryote such as *E. coli* JM101. After the cells are grown, they are plated onto agarose plates and screened using the oligonucleotide primer radiolabeled with $^3$p to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101, as described above.

DNA encoding Htk ligand mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of Htk ligand. While the following discussion refers to DNA, it is understood that the technique also finds application with RNA. The PCR technique generally refers to the following procedure (see Erlich, Science, 252:1643–1650 (1991), the chapter by R. Higuchi, p. 61–70). When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation (s) . This product material is used to replace the corresponding region in the plasmid Chat served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is overlaid with 35 µl mineral oil. The reaction mixture is denatured for five minutes at 100° C., placed briefly on ice, and then 1 µl Thermus aquaticus (Taq) DNA polymerase (5 units/µl, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., Gene, 34:315 (1985). The starting material is the plasmid (or other vector) comprising the Htk ligand DNA to be mutated. The codon(s) in the Htk ligand DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the Htk ligand DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3'and 5'ends that are compatible with the ends of the linearized plasmid, such that it can be directly ligated to the plasmid. This plasmid now contains the mutated Htk ligand DNA sequence.

C. Insertion of Nucleic Acid into Replicable Vector

The nucleic acid (e.g., cDNA or genomic DNA) encoding native or variant Htk ligand is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The Htk ligands of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the Htk ligand DNA that is inserted into the vector. The heterologous signal sequence selected preferably is one that is recognized and processed (i.e., cleaved by a signal peptidase) by the host cell. For prokaryotic host cells that do not recognize and process the native Htk ligand signal sequence, the signal sequence is substituted by a prokaryotic signal sequence selected, for example, from the group of the alkaline phosphatase, penicillinase, lpp, or heat-stable enterotoxin II leaders. For yeast secretion the native signal seqence may be substituted by, e.g., the yeast invertase leader, alpha factor leader (including Saccharomyces and Kluyveromyces α-factor leaders, the latter described in U.S. Pat. No. 5,010, 182 issued 23Apr. 1991), or acid phosphatase leader, the *C. albicans* glucoamylase leader (EP 362,179 published 4 Apr. 1990), or the signal described in WO 90/13646 published 15 Nov. 1990. In mammalian cell expression the native signal sequence (e.g., the Htk ligand presequence that normally directs secretion of Htk ligand from human cells in vivo) is satisfactory, although other mammalian signal sequences may be suitable, such as signal sequences from other animal Htk ligands, and signal sequences from secreted polypeptides of the same or related species, as well as viral secretory leaders, for example, the herpes simplex gD signal.

The DNA for such precursor region is ligated in reading frame to DNA encoding the mature Htk ligand.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gramnegative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of Htk ligand DNA. However, the recovery of genomic DNA encoding Htk ligand is more complex than that of an exogenously replicated vector because restriction enzyme digestion is required to excise the Htk ligand DNA.

(iii) Selection Gene Component

Expression and cloning vectors should contain a selection gene, also termed a selectable marker. This gene encodes a protein necessary for the survival or growth of transformed host cells grown in a selective culture medium. Most cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al., *Science* 209:1422 [1980]) or hygromycin (Sugden et al., *Mol. Cell. Biol.* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the Htk ligand nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Htk ligand. Amplification is the process by which genes in greater demand for the production of a protein critical for growth are reiterated in tandem within the chromosomes of successive generations of recombinant cells. Increased quantities of Htk ligand are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc.*

*Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding Htk ligand. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells [particularly wild-type hosts that contain endogenous DHFR]transformed or co-transformed with DNA sequences encoding Htk ligand, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 [1979]; Kingsman et al., *Gene* 7:141 [1979]; or Tschemper et al., *Gene* 10:157 [1980]). The trp1 gene provides a selection marker for a mutant strain of yeast lacking the ability to grow in tryptophan, for example, ATCC No. 44076 or PEP4-1 (Jones, Genetics 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Bianchi et al., *Curr. Genet.* 12:185 (1987). More recently, an expression system for large-scale production of recombinant calf chymosin was reported for K. lactis. Van den Berg, *Bio/Technology* 8:135 (1990). Stable multicopy expression vectors for secretion of mature recombinant human serum albumin by industrial strains of Kluyveromyces have also been disclosed. Fleer et al., *Bio/Technology* 9:968–975 (1991).

(iv) Promoter Component

Expression and cloning vectors usually contain a promoter that is recognized by the host organism and is operably linked to the Htk ligand nucleic acid. Promoters are untranslated sequences located upstream (5') to the start codon of a structural gene (generally within about 100 to 1000 bp) that control the transcription and translation of particular nucleic acid sequence, such as the Htk ligand nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Htk ligand-encoding DNA by removing the promoter from the source DNA by restriction enzyme digestion and inserting the isolated promoter sequence into the vector. Both the native Htk ligand promoter sequence and many heterologous promoters may be used to direct amplification and/or expression of the Htk ligand DNA. However, heterologous promoters are preferred, as they generally permit greater transcription and higher yields of Htk ligand as compared to the native Htk ligand promoter.

Promoters suitable for use with prokaryotic hosts include the β-lactamase and lactose promoter systems (Chang et al., *Nature* 275:615 [1978]; and Goeddel et al., *Nature* 281:544 [1979]), alkaline phosphatase, a tryptophan (trp) promoter system (Goeddel, *Nucleic Acids Res.*, 8:4057 [1980]and EP 36,776) and hybrid promoters such as the tac promoter (deBoer et al., *Proc. Natl. Acad. Sci. USA* 80:21–25 [1983]). However, other known bacterial promoters are suitable. Their nucleotide sequences have been published, thereby enabling a skilled worker operably to ligate them to DNA encoding Htk ligand (Siebenlist et al., *Cell* 20:269 [1980]) using linkers or adaptors to supply any required restriction sites. Promoters for use in bacterial systems also will contain a Shine-Dalgarno (S.D.) sequence operably linked to the DNA encoding Htk ligand.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3'end of most eukaryotic genes is an AATAAA sequence that may be the signal for addition of the poly A tail to the 3'end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; and Holland, *Biochemistry* 17:4900 [1978]), such as enolase, glyceraldehyde-3phosphate dehydrogenase, hexokinase, pyruvate decarboxylase, phosphofructokinase, glucose-6-phosphate isomerase, 3phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Htk ligand transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Htk ligand sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan and Berg, Science 209:1422–1427 (1980); Pavlakis et al., *Proc. Natl. Acad. Sci. USA* 78:7398–7402 (1981). The immediate early promoter of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc, Natl. Acad. Sci, USA* 79:6777–6781 (1982) on expression of bacterial CAT sequences in CV-1 monkey kidney cells, chicken embryo fibroblasts, Chinese hamster ovary cells, HeLa cells, and mouse NIH-3T 3 cells using the Rous sarcoma virus long terminal repeat as a promoter.

(v) Enhancer Element Component

Transcription of a DNA encoding the Htk ligand of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5'(Laimins et al., *Proc. Natl. Acad. Sci. USA* 78:993 [1981]) and 3'(Lusky et al., *Mol. Cell Bio.* 3:1108 [1983]) to the transcription unit, within an intron (Banerji et al., *Cell* 33:729 [1983]), as well as within the coding sequence itself (Osborne et al., *Mol. Cell Bio.* 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5'or 3'to the Htk ligand-encoding sequence, but is preferably located at a site 5'from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and, for stabilizing the mRNA. Such sequences are commonly available from the 5'and, occasionally 3', untranslated regions of eukaryotic or viral DNAs or cDNAs. These regions contain nucleotide segments transcribed as polyadenylated fragments in the untranslated portion of the mRNA encoding Htk ligand.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

(viii) Transient Expression vectors

Particularly useful in the practice of this invention are expression vectors that provide for the transient expression in mammalian cells of DNA encoding Htk ligand. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Htk ligand that are biologically active Htk ligand.

(ix) suitable Exemplary Vertebrate Cell Vectors

Other methods, vectors, and host cells suitable for adaptation to the synthesis of Htk ligand in recombinant vertebrate cell culture are described in Gething et al., *Nature* 293:620–625 (1981); Mantei et al., *Nature* 281:40–46 (1979); Levinson et al.; EP 117,060; and EP 117,058. A particularly useful plasmid for mammalian cell culture expression of Htk ligand is pRK5 (EP 307,247) or pSVI6B (PCT pub. no. WO 91/08291 published 13 June 1991).

D. Selection and Transformation of Most cells

Suitable host cells for cloning or expressing the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published 12 Apr. 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔptr3 phoAΔE15 Δ (argF-lac)169 ompTΔdegP41kan$^r$. Strain 27C7 was deposited on 30 Oct. 1991 in the American Type Culture Collection as ATCC No. 55,244. Alternatively, the strain of *E. coli* having mutant periplasmic protease disclosed in U.S. Pat. No. 4,946,783 issued 7 Aug. 1990 may be employed. Alternatively, methods of cloning, e.g., PCR or other nucleic acid polymerase reactions, are suitable.

In addition to prokaryotes, eukaryotic microbes such as filamentous fungi or yeast are suitable cloning or expression hosts for Htk ligand-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature* 290:140 [1981]; EP 139,383 published May 2, 1985); Kluyveromyces hosts (U.S. Pat. No. 4,943,529; Fleer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra) , *K. thermotolerans*, and *K. marxianus*; yarrowia [EP 402,226]; *Pichia pastoris* (EP 183,070; Sreekrishna et al., *J. Basic Microbiol.* 28:265–278 [1988]); *Candida; Trichoderma reesia* [EP 244,234]; *Neurospora crassa* (Case et al., *Proc. Natl. Acad. Sci. USA* 76:5259–5263 [1979]); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991) , and Aspergillus hosts such as *A. nidulans* (Ballance et al., *Biochem. Biophys. Res. Commun.* 112:284–289 [1983]; Tilburn et al., *Gene* 26: 205–221 [1983]; Yelton et al., *Proc. Natl. Acad. Sci. USA* 81:1470–1474 [1984]) and *A. niger* (Kelly and Hynes, *EMBO J*, 4:475–479 [1985]

Suitable host cells for the expression of glycosylated Htk ligand are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito) , *Aedes albopictus* (mosquito) , *Drosophila melanogaster* (fruitfly), and *Bombyx mori* have been identified. See, e.g., Luckow et al., *Bio/Technology* 6:47–55 (1988); Miller et al., in *Genetic Engineering*, Setlow et al., eds., Vol. 8 (Plenum Publishing, 1986), pp. 277–279; and Maeda et al., *Nature* 315:592–594 (1985). A variety of viral strains for transfection are publicly available, e.g., the L-1 variant of Autographa californica NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the Htk ligand DNA. During incubation of the plant cell culture with A. tumefaciens, the DNA encoding the Htk ligand is transferred to the plant cell host such that it is transfected, and will, under appropriate conditions, express the Htk ligand DNA. In addition, regulatory and signal sequences compatible with plant cells are available, such as the nopaline synthase promoter and polyadenylation signal sequences. Depicker et al., *J. Mol. Appl. Gen.* 1:561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. USA* 77:4216 [1980]); mouse sertoli cells (TM4, Mather, *Biol. Reprod.* 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad, Sci.* 383:44–68 [1982]); MRC 5 cells; FS4 cells; and a human hepatoma line (Hep G2).

Most cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CAP_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene* 23:315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Viroloqy* 52:456–457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.* 130:946 (1977) and Hsiao et al., *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185: 527–537 (1990), and Mansour et al., *Nature* 336:348–352 (1988).

E. Culturing the Host *Cells*

Prokaryotic cells used to produce the Htk ligand polypeptide of this invention are cultured in suitable media as described generally in Sambrook et al., supra.

The mammalian host cells used to produce the Htk ligand of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace,

*Meth. Enz.* 58:44 (1979), Barnes and Sato, *Anal. Biochem.* 102:255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed., IRL Press, 1991.

The host cells referred to in this disclosure encompass cells in culture as well as cells that are within a host animal.

F. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA* 77:5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.* 75:734–738 (1980).

Antibodies useful for immunohistochemical staining and/or assay of sample fluids may be either monoclonal or polyclonal, and may be prepared in any mammal. Conveniently, the antibodies may be prepared against a native Htk ligand polypeptide or against a synthetic peptide based on the DNA sequences provided herein as described further in Section 4 below.

G. Purification of Htk Ligand Polypeptide

Htk ligand preferably is recovered from the culture medium as a secreted polypeptide, although it also may be recovered from host cell lysates when directly produced without a secretory signal. If the Htk ligand is membrane-bound, it can be released from the membrane using a suitable detergent solution (e.g. Triton-X 100)

When Htk ligand is produced in a recombinant cell other than one of human origin, the Htk ligand is completely free of proteins or polypeptides of human origin. However, it is necessary to purify Htk ligand from recombinant cell proteins or polypeptides to obtain preparations that are substantially homogeneous as to Htk ligand. As a first step, the culture medium or lysate is centrifuged to remove particulate cell debris. Htk ligand thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

In the preferred embodiment, the Htk receptor-Fc fusion disclosed in Bennett et al., supra, is immobilized on a protein A Sepharose column and the Htk ligand can be isolated by affinity purification using this column.

Htk ligand variants in which residues have been deleted, inserted, or substituted are recovered in the same fashion as native Htk ligand, taking account of any substantial changes in properties occasioned by the variation. For example, preparation of a Htk ligand fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-Htk ligand column can be employed to absorb the Htk ligand variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native Htk ligand may require modification to account for changes in the character of Htk ligand or its variants upon expression in recombinant cell culture.

H. Covalent Modifications of Htk Ligand Polypeptides

Covalent modifications of Htk ligand polypeptides are included within the scope of this invention. Both native Htk ligand and amino acid sequence variants of the Htk ligand may be covalently modified. One type of covalent modification included within the scope of this invention is a Htk ligand fragment (e.g. soluble Htk ligand). Variant Htk ligand fragments having up to about 40 amino acid residues may be conveniently prepared by chemical synthesis or by enzymatic or chemical cleavage of the full-length or variant Htk ligand polypeptide. Other types of covalent modifications of the Htk ligand or fragments thereof are introduced into the molecule by reacting targeted amino acid residues of the Htk ligand or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R-N=C=N-R'), where R and R' are different alkyl groups, such as 1-cyclohexyl-3-(2-moropholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking Htk ligand to a water-insoluble support matrix or surface for use in the method for purifying anti-Htk ligand antibodies, and vice-versa. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxy groups of seryl or threonyl residues, methylation of the α-amino groups of lysine, arginine, and histidine side chains (T. E. Creighton, *Proteins: Structure and Molecular Properties*, W. M. Freeman & Co., San Francisco, pp. 79–86 [1983]), acetylation of the N-terminal amine, and amidation of any C-terminal carboxyl group.

Another type of covalent modification of the Htk ligand polypeptide included within the scope of this invention comprises altering the native glycosylation pattern of the polypeptide. By altering is meant deleting one or more carbohydrate moieties found in native Htk ligand, and/or adding one or more glycosylation sites that are not present in the native Htk ligand.

Glycosylation of polypeptides is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Htk ligand polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native Htk ligand sequence (for O-linked glycosylation sites). For ease, the Htk ligand amino acid sequence is preferably altered through changes at the DNA level, particularly by mutating the DNA; encoding the Htk ligand polypeptide at preselected bases such that codons are generated that will translate into the desired amino acids. The DNA mutation(s) may be made using methods described above under the heading of "Amino Acid Sequence Variants of Native Htk Ligand."

Another means of increasing the number of carbohydrate moieties on the Htk ligand polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Blochem.*, pp. 259–306 (1981).

Removal of carbohydrate moieties present on the Htk ligand polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.* 259:52 (1987) and by Edge et al., *Anal. Biochem.* 118:131 (1981). Enzymatic cleavage of carbohydrate moieties on polypeptides can be achieved by the use of a variety of endo- and exo-glycosidases as described by Thotakura et al., *Meth. Enzymol.* 138:350 (1987).

Glycosylation at potential glycosylation sites may be prevented by the use of the compound tunicamycin as described by Duskin et al., *J. Biol. Chem.* 257:3105 (1982). Tunicamycin blocks the formation of protein-N-glycoside linkages.

Another type of covalent modification of Htk ligand comprises linking the Htk ligand polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant Htk ligand, it will be appreciated that some screening of the recovered variant will be needed to select the optimal variant. A change in the immunological character of the Htk ligand molecule, such as affinity for a given antibody, is also able to be measured by a competitive-type immunoassay. The variant is assayed for changes in the suppression or enhancement of its enzymatic activity by comparison to the activity observed for native Htk ligand in the same assay. For example, one can screen for the ability of the variant Htk ligand to stimulate protein kinase activity of the Htk receptor using the techniques set forth in Lokker et al., *EMBO* 11:2503–2510 (1992). See also Example 4 herein. Other potential modifications of protein or polypeptide properties such as redox or thermal stability, hydrophobicity, susceptibility to proteolytic degradation, or the tendency to aggregate with carriers or into multimers are assayed by methods well known in the art.

I. Htk Ligand-Immunoglobulin. Chimeras (Immunoadhesins)

Immunoglobulins (Ig) and certain variants thereof are known and many have been prepared in recombinant cell culture. For example, see U.S. Pat. No. 4,745,055; EP 256,654; Faulkner et al., *Nature* 298:286 (1982); EP 120, 694; EP 125,023; Morrison, *J. Immun.* 123:793 (1979); K öhler et al., *Proc. Nat. Acad. Sci. USA* 77:2197 (1980); Raso et al., *Cancer Res.* 41:2073 (1981); Morrison et al., *Ann. Rev. Immunol.* 2:239 (198); Morrison, *Science* 229:1202 (1985); Morrison et al., *Proc. Natl. Acad. Sci. USA* 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

Chimeras constructed from a receptor sequence linked to an appropriate immunoglobulin constant domain sequence (immunoadhesins) are known in the art. Immunoadhesins reported in the literature include fusions of the T cell receptor (Gascoigne et al., *Proc. Natl. Acad. Sci. USA* 84:2936–2940 [1987]); CD4 (Capon et al., *Nature* 337:525–531 [1989]; Traunecker et al., *Nature* 339:68–70 [1989]; zettmeissl et al., *DNA Cell Biol. USA* 9:347–353 [1990]; and Byrn et al., *Nature* 344: 667–670 [1990]); L-selectin (homing receptor) (Watson et al., *J. Cell. Biol.* 110:2221–2229 [1990]; and Watson et al., *Nature* 349:164–167 [1991]); CD44 (Aruffo et al., *Cell* 61:1303–1313 [1990]); CD28 and B7 (Linsley et al., *J. Exp. Med.* 73:721–730 [1991]); CTLA-4 (Lisley et al., *J. Exp. Med.* 174:561–569 [1991]); CD22 (Stamenkovic et al., *Cell* 66:1133–1144 [1991]); TNF receptor (Ashkenazi et al., *Proc. Natl. Acad. Sci. USA* 88:10535–10539 [1991]; Lesslauer et al., *Eur. J. Immunol.* 27:2883–2886 [1991]; and Peppel et al., *J. Exp. Med.* 174:1483–1489 [1991]); and IgE receptor α (Ridgway and Gorman., *J. Cell. Biol. Vol.* 115, abstr. 1448 [1991]).

The simplest and most straightforward immunoadhesin design combined the binding region(s) of the "adhesin" protein with the hinge and Fc regions of an immunoglobulin heavy chain. Ordinarily, when preparing the Htk ligand-immunoglobulin chimeras of the present invention, nucleic acid encoding the extracellular domain of the Htk ligand, or a fragment thereof, will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity,, secretion, or binding characteristics of the Htk ligand-immunoglobulin chimeras.

In some embodiments, the Htk ligand-immunoglobulin chimeras are assembled as monomers, or hereto- or homo-multimers, and particularly as dimers or tetramers, essentially as illustrated in WO 91/08298.

In a preferred embodiment, the Htk ligand extracellular domain sequence is fused to the N-terminus of the Fc domain of immunoglobulin $G_2$ (IgG-1). It is possible to fuse the entire heavy chain constant region to the Htk ligand extracellular domain sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the Htk ligand amino acid sequence is fused to (a) the hinge region and CH2 and CH3 or (b) the CH1, hinge, CH2 and CH3 domains, of an IgG-1, IgG-2, or IgG-3 heavy chain. The precise site at which the fusion is made is not critical, and the optimal site can be determined by routine experimentation.

In some embodiments, the Htk ligand-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled Htk ligand-immunoglobulin chimeras within the scope herein are schematically diagrammed below:

(a) $AC_L$-$AC_L$;

(b) $AC_H$-[$AC_H$, $AC_L$-$AC_H$, $AC_L$-$V_HC_H$, or $V_LC_L$-$AC_H$];

(c) $AC_L$-$AC_H$-[$AC_L$-$AC_H$, $AC_L$-$V_HC_H$, $V_LC_L$-$AC_H$, or $V_LC_L$-$V_HC_H$];

(d) $AC_L$-$V_HC_H$-[$AC_H$, or $AC_L$-$V_HC_H$, or $V_LV_L$-$AC_H$];

(e) $V_LC_L$-$AC_H$-[$AC_L$-$V_HC_H$, or $V_LC_L$-$AC_H$]; and (f) $[A\text{-}Y]_n$-$[V_LC_L$-$V_HC_H]_2$.

wherein
each A represents identical or different Htk ligand amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the Htk ligand extracellular domain sequences can be inserted between immunoglobulin heavy chain and light chain sequences, such that an immunoglobulin comprising a chimeric heavy chain is obtained. In this embodiment, the Htk ligand sequences are fused to the 3'end of an immunoglobulin heavy chain in each arm of an immunoglobulin, either between the hinge and the CH2 domain, or between the CH2 and CH3 domains. Similar constructs have been reported by Hoogenboom, et al., *Mol. Immunol* 01.28:1027–1037 (1991).

Although the presence of an immunoglobulin light chain is not required in the immunoadhesins of the present invention, an immunoglobulin light chain might be present either covalently associated to an Htk ligand-immunoglobulin heavy chain fusion polypeptide, or directly fused to the Htk ligand extracellular domain. In the former case, DNA encoding an immunoglobulin light chain is typically coexpressed with the DNA encoding the Htk ligand-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger "adhesin" domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For Htk ligand-Ig immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophiis. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites, G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

In designing the Htk ligand-Ig immunoadhesins of the present invention, domains that are not required for rPTK binding and/or biological activity of the Htk ligand may be deleted. With respect to the parental immunoglobulin, a useful joining point is just upstream of the cysteines of the hinge that form the disulfide bonds between the two heavy chains. In a frequently used design, the codon for the C-terminal residue of the "adhesin" (Htk ligand) part of the molecule is placed directly upstream of the codons for the sequence DKTHTCPPCP (SEQ ID NO: 7) of the IgG1 hinge region.

The general methods suitable for the construction and expression of immunoadhesins are the same as those disclosed hereinabove with regard to (native or variant) Htk ligand. Htk ligand-Ig immunoadhesins are most conveniently constructed by fusing the cDNA sequence encoding the Htk ligand portion in-frame to an Ig cDNA sequence. However, fusion to genomic Ig fragments can also be used (see, e.g. Gascoigne et al., supra; Aruffo et al., *Cell* 61:1303–1313 [1990]; and Stamenkovic et al., *Cell* 66:1133–1144 [1991]). The latter type of fusion requires the presence of Ig regulatory sequences for expression. cDNAs encoding IgG heavy chain constant regions can be isolated based on published sequences from cDNA libraries derived from spleen or peripheral blood lymphocytes, by hybridization or by polymerase chain reaction (PCR) techniques. The cDNAs encoding the "adhesin" and the Ig parts of the immunoadhesin are inserted in tandem into a plasmid vector that directs efficient expression in the chosen host cells. For expression in mammalian cells, pRK5-based vectors (Schall et al., *Cell* 61:361–370 [1990]) and CDM8-based vectors (Seed, *Nature 329:840* [*1989*]) are useful. The exact junction can be created by removing the extra sequences between the designed junction codons using oligonucleotide-directed deletional mutagenesis (Zoller and Smith, *Nucleic Acids Res.* 10:6487 [1982]; and Capon et al., *Nature 337:525–531* [*1989*]). Synthetic oligonucleotides can be used, in which each half is complementary to the sequence on either side of the desired junction; ideally, these are 36- to 48-mers. Alternatively, PCR techniques can be used to join the two parts of the molecule in-frame with an appropriate vector.

The choice of host cell line for the expression of Htk ligand-Ig immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell* 61:1303–1313 [1990]; and Zettmeissl et al., *DNA Cell Biol. (US)* 9:347–353 [1990]). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture. These clones are grown in the presence of increasing levels of DHFR inhibitor methotrexate and clones are selected in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells. For example, components such as light chain or J chain may be provided by certain myeloma or hybridoma host cells (Gascoigne et al., supra; and Martin et al., *J. Virol.* 67:3561–3568 [1993]).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol Meth.* 62:1–13 [1983]). Protein G is recommended for all mouse isotypes and for human γ3 (Gusset al., *EMBO J.* 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens and Porath, *Anal. Biochem.* 159:217–226 [1986]) and immobilized metal chelate chromatography (Al-Mashikhi and Makai, *J. Dairy Sci.* 71:1756–1763 [1988]). In contrast to antibodies, however, their behavior on ion exchange columns is dictated not only by their isoelectric points, but also by a charge dipole that may exist in the molecules due to their chimeric nature.

J. Epitope tagged Htk Ligand

This application encompasses chimeric polypeptides comprising Htk ligand fused to another polypeptide (such as the immunoadhesins mentioned above). In one preferred embodiment, the chimeric polypeptide comprises a fusion of the Htk ligand (or a fragment thereof, e.g., the ECD of the Htk ligand) with a tag polypeptide which provides an epitope to which an anti-tag antibody can selectively bind. The epitope tag is generally proved at the amino-or carboxyl- terminus of the Htk ligand. Such epitope tagged forms of the Htk ligand are desirable, as the presence thereof can be detected using a labelled antibody against the tag polypeptide. Also, provision of the epitope tag enables the Htk ligand to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5, (Field et al., *Mol. Cell. Biol.* 8:2159–2165 [1988]); the c-myc tag and the 8F9, 3C7, 6E10, G4, B7 and 9E10 antibodies thereto (Evan et al., *Molecular and Cellular Biology* 5(12):3610–3616 [1985]); and the Herpes Simplex virus glycoprotein D (gD) tag and its antibody (Paborsky et al., *Protein Engineering* 3(6):547–553 [1990]). Other tag polypeptides have been disclosed. Examples include the Flag-peptide (Hopp et al., *BioTechnology* 6:1204–1210 [1988]); the KT3 epitope peptide (Martin et al., *Science* 255:192–194 [1992]); an αtubulin epitope peptide (Skinner et. al., *J. Biol. Chem* 266:15163–15166 [1991]); and the T7 gene 10 protein peptide tag (Lutz-Freyermuth et al., *Proc. Natl. Acad. Sci. USA* 87:6393–6397 [1990]. Once the tag polypeptide has been selected, an antibody thereto can be generated using the techniques disclosed herein.

The general methods suitable for the construction and production of epitope tagged Htk ligand are the same as those disclosed hereinabove with regard to (native or variant) Htk ligand. Htk ligand-tag polypeptide fusions are most conveniently constructed by fusing the cDNA sequence encoding the Htk ligand portion in-frame to the tag polypeptide DNA sequence and expressing the resultant DNA fusion construct in appropriate host cells. Ordinarily, when preparing the Htk ligand-tag polypeptide chimeras of the present invention, nucleic acid encoding the Htk ligand (or a fragment thereof) will be fused at its 3'end to nucleic acid encoding the N-terminus of the tag polypeptide, however 5'fusions are also possible.

Epitope tagged Htk ligand can be conveniently purified by affinity chromatography using the ante-tag antibody. The matrix to which the affinity antibody is attached is most often agarose, but other matrices are available (e.g. controlled pore glass or poly(styrenedivinyl)benzene). The epitope tagged Htk ligand can be eluted from the affinity column by varying the buffer pH or ionic strength or adding chaotropic agents, for example.

2. Therapeutic Uses, Compositions and Administration of Htk Ligand

Htk ligand is believed to find therapeutic use for treating mammals via stimulation or inhibition of growth and/or differentiation and/or activation of cells having a receptor for the Htk ligand, such as the Htk receptor. The prominent regional expression of Htk ligand DNA in the cerebral cortex, hippocampus, striatum, and cerebellum (see Example 3) suggests the possibility that Htk ligand polypeptide might be useful to treat neurodegenerative diseases in which these structures, or neurons projecting to these structures, are affected. Such diseases include, but are not limited to, Alzheimer's disease, Parkinson's disease, Huntington's chorea, and disorders of the cerebellum (Hefti, *J. Neurobiol.* in press [1994]; Marsden, *Lancet* 335:948–952 [1990]; Agid, *Lancet* 337:1321–1327 [1991]; Wexler et al., *Ann. Rev. Neurosci.* 14:503–529 [1991]).

Mature exogenous Htk ligand or a soluble form thereof (e.g., a soluble immunoadhesin) may be administered to a patient in these circumstances. The human Htk ligand is clearly useful insofar as it can be administered to a human having depressed levels of endogenous Htk ligand, preferably in the situation where such depressed levels lead to a pathological disorder.

Therapeutic formulations of Htk ligand are prepared for storage by mixing Htk ligand having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Htk ligand also may be entrapped in microcapsules prepared, for example, by coacervation techniques or by interfacial polymerization (for example, hydroxymethylcellulose or gelatin-microcapsules and poly-[methylmethacylate]microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, supra.

Htk ligand to be used for in vivo administration must be sterile. This is readily accomplished by filtration through sterile filtration membranes, prior to or following lyophilization and reconstitution. Htk ligand ordinarily will be stored in lyophilized form or in solution.

Therapeutic Htk ligand compositions generally are placed into a container having a sterile access port, for example, an intravenous solution bag or vial having a stopper pierceable by a hypodermic injection needle.

The route of Htk ligand administration is in accord with known methods, e.g., injection or infusion by intravenous, intraperitoneal, intracerebral, intramuscular, intraocular, intraarterial, or intralesional routes, or by sustained release systems as noted below. Htk ligand is administered continuously by infusion or by bolus injection. Htk ligand antibody is administered in the same fashion, or by administration into the blood stream or lymph.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels [e.g., poly(2-hydroxyethylmethacrylate) as described by Langer et al., *J. Biomed. Mater. Res.* 15:167–277 (1981) and Langer, *Chem. Tech.* 12:98–105 (1982) or poly (vinylalcohol)], polylactides (U.S. Pat. No. 3,773,919, EP 58,481), copolymers of L-glutamic acid and gamma ethyl-L-glutamate (Sidman et al., *Biopolymers* 22:547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133, 988).

While polymers such as ethylene-vinyl acetate and lactic acidglycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release Htk ligand compositions also include liposomally entrapped Htk ligand. Liposomes containing Htk ligand are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese patent application 83–118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal Htk ligand therapy.

An effective amount of Htk ligand to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 10 mg/kg or more, depending on the factors mentioned above. Typically, the clinician will administer Htk ligand until a dosage is reached that achieves the desired effect. The progress of this therapy is easily monitored by conventional assays.

3. Non-Therapeutic Diagnostic Uses for Htk Ligand

The nucleic acid encoding the Htk ligand may be used as a diagnostic for tissue-specific typing (e.g. mammary gland epithelia). For example, such procedures as in situ hybridization, Northern and Southern blotting, and PCR analysis may be used to determine whether DNA and/or RNA encoding Htk ligand is present in the cell type(s) being evaluated. Htk ligand nucleic acid or polypeptide may also be used as diagnostic markers for mammary gland carcinomas. For example, the Htk ligand may be labeled, using the techniques described herein, and expression of Htk receptor nucleic acid can be quantified, using the labelled Htk ligand.

Human Htk ligand nucleic acid has been localized to chromosome 13q33. Thus, the nucleic acid for human Htk ligand can be used as a marker for this human chromosome.

Htk ligand nucleic acid is also useful for the preparation of Htk ligand polypeptide by recombinant techniques exemplified herein.

isolated Htk ligand polypeptide may be used in quantitative diagnostic assays as a standard or control against which samples containing unknown quantities of Htk ligand may be prepared.

Htk ligand preparations are also useful in generating antibodies, as standards in assays for Htk ligand (e.g., by labeling Htk ligand for use as a standard in a radioimmunoassay, or enzyme-linked immunoassay), for detecting the presence of the Htk receptor in a biological sample (e.g., using a labelled Htk ligand) in affinity purification techniques, and in competitive-type receptor binding assays when labeled with radioiodine, enzymes, fluorophores, spin labels, and the like.

The Htk ligand is also useful as a diagnostic tool. For example, the Htk ligand can be produced in prokaryotic cells using the techniques elaborated herein and the unglycosylated protein so produced can be used as a molecular weight marker, for example. The deduced molecular weight (mw) of the unglycosylated Htk ligand under reducing conditions is about 34 kD. Soluble Htk ligand has a deduced mw of 22 kD under reducing conditions. In order to use Htk ligand as a molecular weight marker, gel filtration chromatography or SDS-PAGE, for example, will be used to separate protein(s) for which it is desired to determine their molecular weight(s) in substantially the normal way. The Htk ligand and other molecular weight markers will be used as standards to provide a range of molecular weights. For example, phosphorylase b (mw=97,400), bovine serum albumin (mw=68,000), ovalbumin (mw=46,000), Htk ligand (mw=34,000), trypsin inhibitor (mw=20,100), and lysozyme (mw=14,400) can be used a mw markers. The other molecular weight markers mentioned here can be purchased commercially from Amersham Corporation, Arlington Heights, IL, for example. Often, the molecular weight markers will be labelled to enable easy detection following separation. Techniques for labelling antibodies and proteins are discussed herein and are well known in the art. For example, the molecular weight markers may be biotinylated and, following separation on SDS-PAGE, for example, the blot can be incubated with streptavidin-horseradish peroxidase. The bands can then be detected by light detection.

It may also be useful to grow certain cells having the Htk receptor ex vivo using the Htk ligand as a growth factor. These cells which are to be grown ex vivo may simultaneously be exposed to other known growth factors or cytokines. Exemplary cytokines include the interleukins (e.g., IL-3), granulocyte-macrophage colony-stimulating factor (GM-CSF), macrophage colony-stimulating factor (M-CSF), granulocyte colony-stimulating factor (GM-CSF), erythropoietin (Epo), lymphotoxin, steel factor (SLF), tumor necrosis factor (TNF) and gamma-interferon. This results in proliferation and/or differentiation of the cells having the Htk receptor. For example, human tumor cell lines for which it is desired to isolate certain tumor associated factors (usually proteins) therefrom may be grown ex vivo using the Htk ligand. Also, antibodies against the tumor associated factors can be generated which may be useful for diagnostic purposes. Examples of such tumor cell lines which can be treated with the Htk ligand include mammary cancer cells (e.g. MCF-7), liver cell lines, Colo 205, NCI 69, HM-1 and HeLa, for example.

In yet another aspect of the invention, the ligand may be used for affinity purification of the Htk receptor. Briefly, this technique involves covalently attaching the Htk ligand to an inert and porous matrix (e.g., agarose reacted with cyanogen bromide). A solution containing the Htk receptor can then be passed through the chromatographic material and can be subsequently released by changing the elution conditions (e.g. by changing pH or ionic strength).

The purified Htk ligand, and the nucleic acid encoding it, may also be sold as reagents for mechanism studies of the ligand and its cognate receptor, to study the role of the Htk ligand and receptor in normal growth and development, as well as abnormal growth and development, e.g. in malignancies.

Htk ligand may be used for competitive screening of potential agonists or antagonists for binding to the Htk receptor. Htk ligand variants are useful as standards or controls in assays for Htk ligand, provided that they are recognized by the analytical system employed, e.g. an anti-Htk ligand antibody.

4. Htk ligand Antibody Preparation

A description follows as to the production of exemplary antibodies as defined herein. These exemplary antibodies include polyclonal, monoclonal, humanized, bispecific or heteroconjugate antibodies.

A. Polyclonal Antibodies

Polyclonal antibodies to the Htk ligand generally are raised in animals by multiple subcutaneous (sc) or intraperitoneal (ip) injections of the Htk ligand and an adjuvant. It may be useful to conjugate the Htk ligand or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg of 1 µg of conjugate (for rabbits or mice, respectively) with 3 volumes of Freud's complete adjuvant and injecting the solution intradermally at multiple sites. One month later the animals are boosted with ⅕ to ⅒ the original amount of conjugate in Freud's complete adjuvant by subcutaneous injection at multiple sites. 7 to 14 days later the animals are bled and the serum is assayed for anti-Htk ligand antibody titer. Animals are boosted until the titer plateaus. Preferably, the animal is boosted with the conjugate of the same Htk ligand, but conjugated to a different protein and/or through a different cross-linking reagent. Conjugates also can be made in recombinant cell culture as protein fusions. Also, aggregating agents such as alum are used to enhance the immune response.

B. Monoclonal Antibodic

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-Htk ligand monoclonal antibodies of the invention may be made using the hybridoma method first described by Kohler & Milstein, Nature 256:495 (1975), or may be made by recombinant DNA methods (Cabilly et al., U.S. Pat. No. 4,816,567).

In the hybridoma method, a mouse or other appropriate host animal, such as hamster, is immunized as hereinabove described to elicit lymphocytes that produce, or are capable of producing, antibodies that will specifically bind to the protein used for immunization. Alternatively, lymphocytes may be immunized in vitro. Lymphocytes then are fused/ with myeloma cells using a suitable fusing agent, such as polyethylene glycol, to form a hybridoma cell (Goding, Monoclonal Antibodies: Principles and Practice, pp.59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 [1984]; and Brodeur et al., *Monoclonal Antibody Production Techniques and Applications*, pp. 51–63, Marcel Dekker, Inc., N.Y., 1987). See, also, Boerner et al., *J. Immunol.*, 147(1):86–95 (1991) and WO 91/17769, published Nov. 28, 1991, for techniques for the production of human monoclonal antibodies.

Culture medium in which hybridoma cells are growing is assayed for production of monoclonal antibodies directed against Htk ligand. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, *Anal. Biochem.* 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Practice.*, pp. 59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90:2551–255 (1993); and Jakobovits et al., *Nature* 362:255–258 (1993).

In a further embodiment, antibodies or antibody fragments can be isolated from antibody phage libraries generated using the techniques described in McCafferty et al., *Nature*, 348:552–554 (1990), using the Htk ligand (or a fragment thereof) to select for a suitable antibody or antibody fragment. Clackson et al., *Nature*, 52:624–628 (1991) and Marks et al., *J. Mol. Biol.* 222:581–597 (1991) describe the isolation of murine and human antibodies, respectively, using phage libraries. Subsequent publications describe the production of high affinity (nM range) human antibodies by chain shuffling (Mark et al., *Bio./Technol* 10:779–783 [1992]), as well as combinatorial infection and in vivo recombination as a strategy for constructing very large phage libraries (Waterhouse et al., *Nuc. Acids Res.*, 21:2265–2266 [1993]). Thus, these techniques are viable alternatives to traditional monoclonal antibody hybridoma techniques for isolation of "monoclonal" antibodies (especially, human antibodies) which are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary, (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-Htk ligand monoclonal antibody herein.

Typically, such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for an Htk ligand and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope such as $^3H$, $^{14}C$, $^{32}P$, $^{35}S$, or $^{125}I$; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for separately conjugating the antibody to the detectable moiety may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be an Htk ligand, or an immunologically reactive portion thereof) to compete with the test sample analyte (Htk ligand) for binding with a limited amount of antibody. The amount of Htk ligand in the test sample is inversely proportional to the amount of standard that becomes bound to the antibodies. To facilitate determining the amount of standard that becomes bound, the antibodies generally are insolulbilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522–525 [1986]; Riechmann et al., *Nature* 332:323–327 [1988]; Verhoeyen et al., *Science* 239:1534–1536 [1988]), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues, and possibly some FR residues, are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see WO 92/22653, published Dec 23, 1992.

D. Bispecific Antibodies

Bispecific antibodies are monoclonal, preferably human or humanized, antibodies that have binding specificities for at least two different antigens. In the present case, one of the binding specificities is for a Htk ligand, the other one is for any other antigen, and preferably for a receptor or receptor subunit. For example, bispecific antibodies specifically binding a Htk receptor and Htk ligand are within the scope of the present invention.

Methods for making bispecific antibodies are known in the art. Traditionally, the recombinant production of bispecific antibodies is based on the coexpression of two immunoglobulin heavy chain/light chain pairs, where the two heavy chains have different specificities (Millstein and Cuello, *Nature* 305:537–539 [1983]). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, published 13 May 1993, and in Traunecker et al., *EMBO* 10:3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology* 121:210 (1986).

E. Heteroconjugate Antibodies.

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

5. Uses of Htk ligand Antibodies

Htk antibodies may be useful in certain therapeutic indications to block activity of the Htk ligand (for example in mammary carcinogenesis).

Therapeutic Htk ligand antibody formulations and modes for administration will be similar to those described above for Htk ligand. A typical daily dosage of the antibody might range from about 1 µg/kg to up to 5 mg/kg or more, depending on the factors mentioned above for Htk ligand administration.

Htk ligand antibodies may also be useful in diagnostic assays for Htk ligand, e.g., detecting its expression in specific cells, tissues, or serum. The antibodies are labeled in the same fashion as Htk ligand described above and/or are immobilized on an insoluble matrix. Htk ligand antibodies also are useful for the affinity purification of Htk ligand from recombinant cell culture or natural sources. Htk ligand antibodies that do not detectably cross-react with other proteins can be used to purify Htk ligand free from these other known proteins. Suitable diagnostic assays for Htk ligand and its antibodies are described above.

III. Experimental

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLE 1

Production of a Soluble Htk Receptor-Fc Fusion Protein for the Identification of Htk ligand In order to identify and ultimately clone the Htk ligand, a fusion protein is constructed which consists of the extracellular domain (ECD) of the Htk receptor fused to human $IgG_1$ Fc. See Bennett et al., supra for techniques for the production of the fusion protein.

The Htk receptor-Fc fusion is used to screen a series of kidney cell lines for their capacity to bind the extracellular domain of the Htk receptor, using FACS analysis, as previously described. See Urdal et al., *J. Biol. Chem.* 63:2870–2877 (1988); and Gearing et al., *EMBO J.* 8:3667–3676 (1989). Any cell line specifically binding the fusion protein is indicative of a membrane bound or membrane associated source of the Htk ligand. Screening of some 15 kidney cell lines results in the discovery of specific binding to one murine kidney mesangial cell line termed SV40MES 13. The SV40MES 13 cell line is demonstrated to be positive for Htk-Fc binding and not for other Fc fusion proteins.

Binding competition studies are performed as follows. SV40MES 13 cells ($5\times10^6$ cells per well) are assayed for steady-state binding of $^{125}$I-Htk-Fc in the presence of varying amounts of unlabelled Htk-Fc. The cells are incubated with 1 nM or 0.2 nM $^{125}$I-Htk-Fc and various concentrations of unlabelled Htk-Fc (10 pm -1 µM) for 2 hr. at 4° C. Cells and unbound $^{125}$I-labelled Htk-Fc are separated by centrifugation through a sucrose cushion as previously described in Lee et al., *J. Biol. Chem.* 267:16283–16287 (1992). The binding data are analyzed to determine the affinity and number of sites per cell as described in Munson and Rodbard *Anal. Biochem.* 107:220–239 (1980). Htk-Fc fusion protein is iodinated by the lactoperoxidase method as described in Urdal et al., *J. Biol. Chem.* 263:2870–2877 (1988). The $K_d$ for fusion protein binding to SV40MES 13 is 3 nM with approximately 6,500 sites per cell (FIG. 5A). Conditioned media from the SV4OMES 13 cell line is unable to activate tyrosine autophosphorylation of the Htk receptor, supporting the concept of a membrane bound ligand.

EXAMPLE 2

Cloning the Murine Htk Ligand

The Htk receptor-Fc protein is used to expression clone the Htk ligand from an SV40MES 13 cDNA library transiently transfected into COS-7 cells, as follows. A cDNA expression library from the SV40MES 13 cell line is constructed in the plasmid vector pRK5B (Holmes et al., *Science* 253:1278–1280 [1991]). Fifty pools of approximately 2000 cDNAs each are initially transfected into COS-7 cells and the cells are screened for the capacity to bind Htk receptor-Fc, using slide autoradiography, as described in Gearing et al., *EMBO* 8:3667–3676 (1989). Five positive pools result from this initial screen and two of these pools are gradually subdivided in successive rounds of screening until individual clones are obtained.

Binding competition experiments are performed using one of the positive clones (#7), termed murine pRK5B-Htk ligand. In particular, binding competition curves are generated as described above with respect to SV40MES 13, using monolayers of COS-7 cells ($5\times10^5$ cells per well) which are transiently transfected with clone #7, using the DEAE Dextran transfection method (McMahan et al., *EMBO J.* 10:2821–2830 [1991]).

Figure 5B:
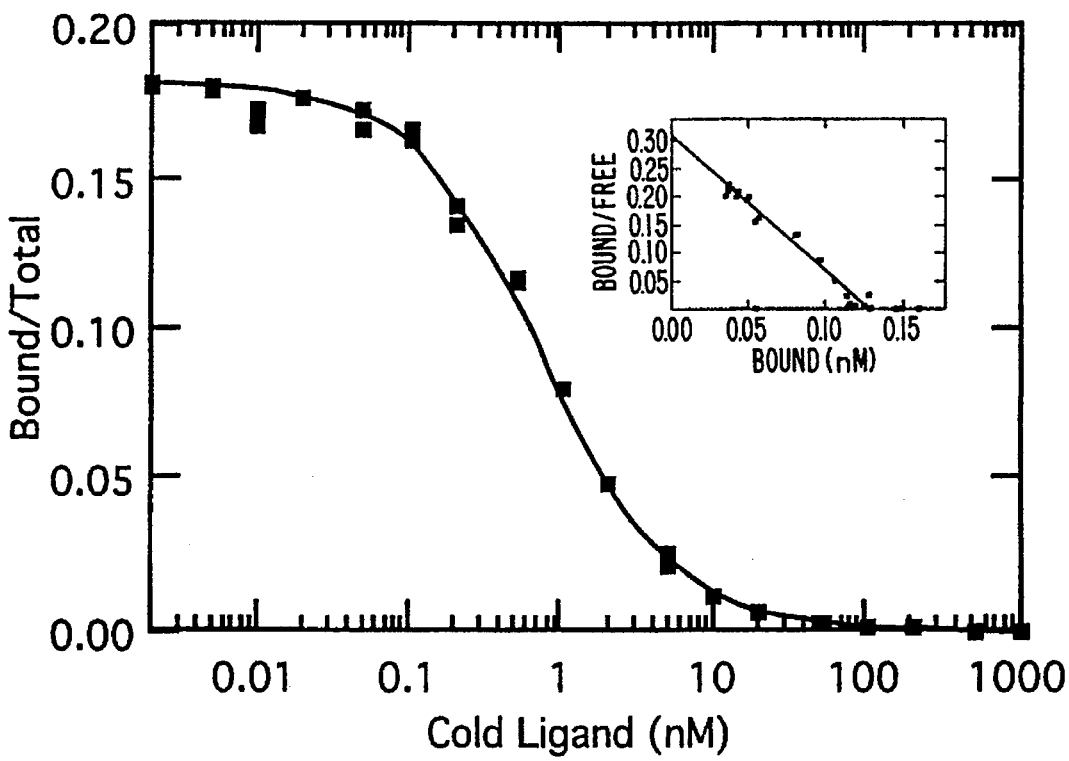

Transfected COS-7 cells (COS-7t) used at $2.5\times10^4$ cells per binding point are assayed for steady-state binding of $^{125}$I-Htk-Fc in the presence of varying amounts of unlabelled Htk-Fc, as described above. Htk-Fc binding to transfected COS-7 cells demonstrates a $K_d$ of 500 pm (FIG. 5B), indicating that clone #7 is the murine Htk-ligand.

The DNA sequence and deduced amino acid sequence of the murine Htk ligand are shown in FIGS. 1A-B. The predicted molecular weight of the protein following signal peptide cleavage is 34 kD with an estimated pI of 8.9.

The sequence derived from the #7 clone is confirmed by sequencing another independent clone of 4700 bp that gives the identical coding sequence. DNA sequencing is performed using the ABI Taq Dye Deoxy terminator cycle sequencing kit on an automated Applied Biosystems DNA sequencer, model 373A. Both strands of individual clones are sequenced in their entirety.

sequence comparison of the Htk ligand and B61 (Bartley et al., supra and Holzman et al., supra) indicates 23% similarity between the molecules. However, B61 does not contain a transmembrane domain. Nevertheless, the degree of homology suggests that the Htk ligand and B61 may comprise members of a structurally similar family that bind to various members of the EPH/ELK family of receptor tyrosine kinases.

EXAMPLE 3

Tissue Distribution of the Htk ligand

Northern blot analysis is performed in order to detect the presence of the Htk ligand in mouse adult tissues, human adult tissues and human fetal tissues. In particular, Northern blots are obtained from Clonetech (Palo Alto, Calif.) which contain 2 μg/lane of polyA-selected RNA from mouse adult, human adult and human fetal tissues. Mouse blots are hybridized in 50% formamide at 42° C. to $^{32}$P labelled murine Htk ligand cDNA and washed under stringent conditions (final wash: 0.2×SSC, 0.2% SDS at 60° C.). Human tissue blots are hybridized in 35% formamide at 42° C. and washed under stringent conditions as above.

Northern analysis of mouse and human Htk ligand messenger RNA in adult and fetal tissues shows only one transcript at approximately 5.2 kb which displays widespread tissue expression. In particular, the Htk ligand is present in large amounts in mouse adult lung, brain, heart and kidney,, and in lesser amounts in spleen, liver, skeletal muscle and testis. The ligand is present in human adult heart, brain, placenta, lung, liver, skeletal muscle, kidney, pancreas, spleen, thymus, prostate, testis, ovary, small intestine and colon but is not detectable by Northern analysis in peripheral blood leukocytes. Finally, the transcript is detectable in highest amounts in human fetal brain, lung, and kidney tissues with lower amounts detectable in human fetal liver tissue.

In situ hybridizations are also performed to detect Htk ligand DNA expression. Mouse embryos (embryonic day 13) or brains from postnatal day one or adult mice are prepared for in situ hybridization as follows. Freshly dissected brains or embryos fixed in 4% formaldehyde are frozen and sectioned with a cryostat. Sections are thaw-mounted onto slides, air dried, and stored at −70° C. Hybridization is conducted with $^{32}$P-labelled riboprobes by a modification of published methods (Phillips et al., *Science* 250:290–294 [1990]). Sense (control) and antisense cRNA probes corresponding to nucleotides 1597 to 2198 of the murine Htk ligand DNA sequence of FIGS. 1A–B are utilized for hybridization.

On the day of hybridization, sections are brought to room temperature, fixed for 10–30 minutes in 4% formaldehyde with or without the addition of 1% glutaraldehyde in 0.1M phosphate (pH 7.2), rinsed, and incubated in hybridization buffer for 1–3 hours at 42° C. Hybridization buffer consists of 50% formamide, 0.1M NaCl, 20mM Tris HCl, pH 8.0, 1×Denhardt's solution, 10% Dextran sulfate, 10mM DTT. Probes are heated to 95° C. for 3 minutes in the presence of carrier RNA, after which they are immediately cooled to 4° C. Probe is then added to the hybridization buffer on each slide at a final concentration of 6.5×10$^6$ cpm/ml, and allowed to hybridize at 55° C. overnight. Following hybridization, sections are treated as follows: 2 rinses in 2×SSC, 30 minute incubation in RNAse A (20 μg/ml), 2 rinses in 2×SSC, 1 hour incubation at 55° C. in 0.1×SSC, 2 rinses in 0.5×SSC, dehydration in a series of graded ethanol solutions (60%, 75%, and 85% ethanol containing 0.3M ammonium acetate, followed by 90% and 100% ethanol), and air drying at room temperature. The sections are then exposed to sheet film (Beta-Max, Amersham) for a period of 1 to 3 days after which they are dipped in emulsion (Amersham LM-1) and exposed at 4° C. for 3 to 8 weeks. Film and emulsion autoradiographs are developed by treatment with standard photographic developer and fixer.

The sheet film autoradiographs are viewed both by visual inspection on a light box and through a stereoscopic microscope. The emulsion autoradiographs are viewed under both brightfield and darkfield microscopy. Observation of the autoradiograms reveals hybridization signal in several regions on the sections hybridized with antisense probe that were not observed on the control sections hybridized with sense probe. These regions include, but are not restricted to, several regions of the adult forebrain, including the CA1 region of the hippocampus, the cerebral cortex (including piriform and entorhinal cortices), and the caudate-putamen. Prominent hybridization is also observed in the cerebellar cortex. Hybridization is less intense or absent from other brain structures including the septum, white matter tracts such as the corpus callosum, and numerous diencephalic, mesencephalic, and myelencephalic regions. In the embryo, strong hybridization is seen in (but not confined to) the developing lung, digestive tract, liver, kidney, salivary gland, vertebrae, muscle, olfactory epithelium, epithelium of developing ear, within both dorsal root and trigeminal ganglia, meninges of both brain and spinal cord, and within numerous regions of both brain and spinal cord. Within the developing brain, expression is notably intense in the developing forebrain, but significant hybridization was observed in all major subdivisions (telencephalon, diencephalon, mesencephalon, metencephalon, and myelencephalon).

EXAMPLE 4

Induction of Tyrosine Phosphorylation of the Htk Receptor by the Ligand

To determine whether the Htk ligand stimulates Htk phosphorylation, and to further confirm that clone #7 described above indeed codes for a ligand for the Htk receptor, the following experiment is performed.

NIH 3T3 cells are stably transferred with the full-length Htk receptor. A 4038 bp ClaI - XbaI cDNA fragment containing 32 bp of linker sequence, 37 bp of pBluescript (Stratagene La Jolla, Calif.) polylinker and the entire 3969 bp Htk receptor cDNA is subcloned into the expression vector pRIS (Genentech, Inc.) under the control of the Rous sarcoma virus LTR promoter. NIH3T3 cells maintained in high glucose Dulbecco's Modified Eagle's Medium (DMEM) supplemented with 10% FCS are co-transfected with pRIS-Htk receptor and pNeo (an SV40 based vector containing the neomycin resistance marker) by the calcium phosphate method as described by Gorman et al., in *DNA Prot. Engineer. Tech.* 2:3–10 [1990]. Neomycin resistant colonies are selected 48 hours after transfection with Geneticin (Gibco/BRL) at 400 μg/ml. Fourteen days later individual resistant colonies are isolated, expanded and analyzed by flow cytometry for Htk receptor expression using rabbit polyclonal antiserum. Specificity of response is demonstrated using mock-transfected 3T3 cells.

Then, one million transfected 3T3 cells (3T3-T) or non-transfected 3T3 cells (3T3) are co-incubated with 1×10$^6$ Htk ligand transiently transfected COS-7 cells (transfected with clone #7 from above using the DEAE-dextran method as described above), mock-transfected COS-7 cells, or 3×10$^6$ SV40MES 13 cells, at 37° C. for 30 minutes. Transfected and mock transfected NIH 3T3 cells are also incubated with monoclonal anti-human Htk receptor antibody (IC2-C2) produced by hybridoma Anti-HpTK 5 (ATCC Accession No. HB 11,583), known to induce autophosphorylation of the Htk receptor.

Cells are lysed in NP-40 lysis buffer (1% NP-40, 1 mM EDTA, 200 mM NaCl, 50 mM Tris Cl, pH 8.0, 2 mM DMSF, 2.5 mM Na$_3$VO$_4$) and immunoprecipitated with anti-human Htk rabbit polyclonal sera, produced as follows. Polyclonal antibodies are generated in New Zealand White rabbits against the soluble Htk receptor-Fc fusion protein described in Bennett et al., supra. 4 μg of the protein in 100 μl PBS is emulsified with 100 μl Freund's adjuvant (complete adjuvant for the primary injection and incomplete adjuvant for all boosts). For the primary immunization and the first boost, the protein is injected directly into the popliteal lymph nodes (Sigel et al., *Methods Enzymol.* 93:3–12 [1983]). For subsequent boosts, the protein is injected into subcutaneous and intramuscular sites. 1.3 µg protein/kg body weight is injected every 3 weeks with bleeds taken 1 and 2 weeks following each boost. Specificity of the antibody is demonstrated by flow cytometric analysis of NIH3T3 cells transfected with full length Htk receptor or vector alone using a 1:200 dilution of the pre-immune serum or anti-Htk receptor-IgG Fc serum.

Immunoprecipitated cells are analyzed on SDS-PAGE 4–12% gradient gels. Gels are then transferred to nitrocellulose filters and Western blotted using the antiphosphotyrosine antibody 4G10 (UBI, Lake Placid, N.Y.). Both clone #7 transfected COS-7 cells, SV40MES 13 cells, and IC2-C2 antibody induce autophosphorylation of the Htk receptor upon coincubation, confirming that the Htk ligand stimulates Htk phosphorylation and that clone #7 codes for a Htk ligand.

EXAMPLE 5

Cloning the Human Htk ligand

In order to clone the human Htk ligand, a human fetal brain cDNA library is prepared using the techniques generally described in Sambrook et al., supra. A human fetal lung library is purchased from Clonetech (Palo Alto, Calif.). These libraries are screened using techniques described in Sambrook et al., supra, with a fragment from the 5'end of the mouse cDNA as a probe (i.e., residues 515 to 2,312 of FIGS. 1A-B). The entire human Htk ligand gene is found to be present in a single clone isolated from the human fetal brain library. The plasmid having the nucleic acid encoding the human Htk ligand has been deposited with the American Type Culture Collection (ATCC) on Jun. 24, 1994 under Accession No. 75,820. The nucleotide and amino acid sequences of the human Htk ligand are shown in FIG. 2. The sequence encodes a protein having a predicted molecular weight of 34kD following signal peptide cleavage. The murine and human ligands show 96% sequence identity at the amino acid level, demonstrating a high degree of conservation between species. This is consistent with the homology between human Htk receptor and its mouse homologue, myk-1, which are 91% identical at the amino acid level.

Deposits

The following cultures have been deposited with the American Type Culture Collection, 12301 Parklawn Drive, Rockville, Md., USA (ATCC):

| Hybridoma | ATCC No. | Deposit Date |
|---|---|---|
| Anti-HpTK5 | HB 11,583 | March 15, 1994 |
| Plasmid Human Htk Ligand | ATCC 75,820 | June 24, 1994 |

These deposits were made under the provisions of the Budapest Treaty on the International Recognition of the Deposit of Microorganisms for the Purpose of Pat. Procedure and the Regulations thereunder (Budapest Treaty). This assures maintenance of viable cultures for 30 years from the date of deposit. The deposits will be made available by ATCC under the terms of the Budapest Treaty, and subject to an agreement between Genentech, Inc. and ATCC, which assures permanent and unrestricted availability of the cultures to the public upon issuance of the pertinent U.S. patent or upon laying open to the public of any U.S. or foreign patent application, whichever comes first, and assures availability of the cultures to one determined by the U.S. Commissioner of Patents and Trademarks to be entitled thereto according to 35 USC §122 and the Commissioner's rules pursuant thereto (including 37 CFR §1.14 with particular reference to 886 0G 638).

The assignee of the present application has agreed that if the cultures should die or be lost or destroyed when cultivated under suitable conditions, they will be promptly replaced on notification with a viable specimen of the same culture. Availability of the deposited strains is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiment is intended as a single illustration of one aspect of the invention and any cultures that are functionally equivalent are within the scope of this invention. The deposit of materials herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

We claim:

1. A method for activating a tyrosine kinase domain of a hepatoma transmembrane kinase receptor (Htk receptor) comprising the step of binding an isolated hepatoma transmembrane kinase receptor ligand to an extracellular domain of the Htk receptor, wherein said receptor ligand comprises an amino acid sequence selected from the group consisting of:

(a) the amino acid sequence for mature murine Htk ligand of SEQ ID NO: 2;

(b) the amino acid sequence for mature human Htk ligand of SEQ ID NO: 4;

(c) the naturally occurring amino acid sequence for mature Htk ligand from an animal species other than those sequences of (a) or (b);

(d) allelic variants of the sequences of (a), (b), or (c); and (e) the sequences of (a), (b), (c) or (d) having a single preferred conservative amino acid substitution as defined in Table 1.

2. A method for activating a tyrosine kinase domain of a hepatoma transmembrane kinase receptor (Htk receptor) comprising the step of binding a soluble hepatoma transmembrane kinase receptor ligand to an extracellular domain of the Htk receptor wherein said receptor ligand comprises an amino acid sequence selected from the group consisting of:

(a) the amino acid sequence for mature soluble murine Htk ligand, wherein said amino acid sequence for mature soluble murine Htk ligand is amino acids 28-227 of SEQ ID NO: 2;

(b) the amino acid sequence for mature soluble human Htk ligand, wherein said amino acid sequence for mature soluble human Htk ligand is amino acids 25-224 of SEQ ID NO: 4;

(c) the naturally occurring amino acid sequence for mature soluble Htk ligand from an animal species other than those sequences of (a) or (b);

(d) allelic variants of the sequences of (a), (b), or (c); and (e) the sequences of (a), (b), (c), or (d) having a single preferred conservative amino acid substitution as defined in Table 1.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 4342 bases
( B ) TYPE: nucleic acid ( C ) STRANDEDNESS: single
( D ) TOPOLOGY: linear ( x i ) SEQUENCE DESCRIPTION: SEQ ID NO:1:

```
CCCACGCGTC CGCGCGCGCT GAGGGACGCG CAGGGTGAGC GCACCTGGCC    50
TCGGCGACCG CGGGAGCGGC GCGGCGTGTC CGCCCCGGAG GATTGGGGGT   100
CGCTGCCCGC GGCCGGTCCC AACGCGTCCC GGAGTGCGCA GAACTGGGAG   150
CGGCTTGGGC ATGGCCATGG CCCGGTCCAG GAGGGACTCT GTGTGGAAGT   200
ACTGTTGGGG ACTTTTGATG GTTTTGTGCA GAACTGCGAT CTCCAGATCG   250
ATAGTTTTAG AGCCTATCTA CTGGAATTCC TCGAACTCCA AATTTCTACC   300
CGGACAAGGC CTGGTACTAT ACCCACAGAT AGGAGACAAA TTGGATATTA   350
TTTGCCCCAA AGTGGACTCT AAAACTGTTG GCCAGTATGA ATATTATAAA   400
GTTTATATGG TTGATAAAGA CCAAGCAGAC AGATGCACAA TTAAGAAGGA   450
GAATACCCCG CTGCTCAACT GTGCCAGACC AGACCAAGAT GTGAAATTCA   500
CCATCAAGTT TCAAGAATTC AGCCCTAACC TCTGGGGTCT AGAATTTCAG   550
AAGAACAAAG ATTACTACAT TATATCTACA TCAAATGGGT CTTTGGAGGG   600
CCTGGATAAC CAGGAGGGAG GGGTGTGCCA GACAAGAGCC ATGAAGATCC   650
TCATGAAAGT TGGACAAGAT GCAAGTTCTG CTGGATCAGC CAGGAATCAC   700
GGTCCAACAA GACGTCCAGA GCTAGAAGCT GGTACAAATG GGAGAAGTTC   750
AACAACAAGT CCCTTTGTGA AGCCAAATCC AGGTTCTAGC ACCGATGGCA   800
ACAGCGCGGG GCATTCCGGG AACAATCTCC TGGGTTCCGA AGTGGCCTTA   850
TTCGCAGGGA TCGCATCAGG ATGCATCATC TTCATCGTCA TCATCATCAC   900
TTTGGTGGTG CTGCTGCTCA AGTACCGCAG GAGACACCGC AAACACTCTC   950
CACAGCACAC GACCACGCTG TCTCTCAGCA CACTGGCCAC GCCCAAGCGA  1000
GGTGGCAACA ACAATGGCTC GGAGCCCAGT GACGTTATCA TACCACTAAG  1050
GACTGCAGAC AGCGTCTTCT GCCCGCACTA CGAGAAGGTC AGCGGGGACT  1100
ATGGGCACCC GGTGTACATC GTGCAGGAGA TGCCCCCACA GAGTCCTGCC  1150
AACATTTACT ACAAGGTCTG AGGCCTGAGA CCTGCGCCTC CAAGGGAAC   1200
TCGCACCTTG TTCTTGGGCA CGCAGGGACT GCCTGAGCCT GGCTGTGGGG  1250
GCAGGATGCC TCCTGGAAGA GCCTGGATCT GGACAGTTTT GTAGTCTGTA  1300
GCTTTTCCGA CCCTGGGGAC CACAGACCCT CCCCGGAAGC TGGAAGACTG  1350
CTAGGAGATC CCCACTTGGA CTGCCGCGGC CCCACGCGGA CCTCCAAGCC  1400
ATGCACCCAG CCACTCAGGC CTCTGCAGAG CCCGGGGAGG ACACGGTAGG  1450
CTATGGATGG CGCAGCAGCA TCTTAGGAGA AGGTTGCGCA CCAGGCCGGC  1500
CCCTGCCTCC ACGTTTCCTG CCGTGCACAC TGGACTTATC ACTTGGACCT  1550
CGGGTTCAGT AAGGTTTTCA AAGATCTCTA GTGTTTAGTC CTCACTCACT  1600
CACTCACTCA CTCACTCCTT CTCTTGCCAG GGCTCTGCAG CAAACTCCCT  1650
AGACCCCTCA CTCCACGTAC TGCATCATTA CGGGACACTC ACCACAGAGT  1700
CCCAGCTCCA CCCTTTACAC CAAGATCAAA TTAGATGGGT ATTAGGTACA  1750
GAAGAACCCT GCTTGCCTGG AGGCCGGGTC AGCCGGGAAG CGCAGATGTG  1800
TGGAGGAGTG AGGAGGTGCT GGCTGCCACG GCAGGTCAAG GCTGCTTGCT  1850
GCCCCTGGAG CATAGTAGGG ATGCAGGAAG GAAATAGATA ATGCTTTGGT  1900
```

```
TTTTCTGAGA  GGACAGAGAC  AGGTGGGAGG  TGACTGACTG  GTGAGTGGTG  1950
GGGAGCCTTT  CACTACCACA  CAGCTATGCA  GCAGGGAATC  AAAAGTCCCT  2000
CTCCTGCGGG  GAACAAAGGG  GCCATTGTTG  TGAAAGGACC  AGCTAGAGCA  2050
CAGAGGGAGA  GGGCAGGCCT  CCGGTGAAGT  GCTGGGCAG   AACTGCAGAG  2100
GTACTGGAAA  TAAAAAGCGC  AGCGCAGAGC  TGTGGGAGAG  TCCGTCTGCT  2150
TTGGGAGATG  TTTTAAGCAG  ACTCAGCTGC  TATATTACCA  CGTTTTTATT  2200
AAAAACACAG  GGAAAGCATT  TAGGAGAAGA  GCAGAGAGCC  AAATCTGACC  2250
TAGAAGTTGA  AAAGCCAAAG  GTCAAACAGG  CTGTAAGTCC  ATCACCACTG  2300
AGGTTATTGG  AGAATTCTCA  TTAGGAAAGG  CAGGTCAGAT  TCCCCAGGCC  2350
CCATAAGTGC  CCCTTCCCCC  TCCCTGATTG  AGCCTTACAC  GTTGGTTTTT  2400
GGTTTATGGC  CGTGCTGTCC  GGGCTCCAAG  GCAGTACCCG  GGCTCCATGT  2450
CAAAGCAAAG  CACACATGGC  CCACCTCTTA  GAGTCCTTGA  GATGGAAGTA  2500
AGTTATGCCG  CGGAAGGAAA  GGCGAAGATA  GGACATATTT  ATAATAGGTG  2550
TATAGAACAC  AAGGGATATA  AAATGAAAGA  TTTTACTAA   TATATATTTT  2600
AAGATTACAC  ACAATACACA  CCAGAAGACG  TGGAGTTCGG  TGGTGGTGGT  2650
GGTCGTGGTG  GTGGTGATTA  AAGTGACCCC  AGCGCTTAGT  GCTTTAAAAA  2700
GTGAAAGATT  GGGTAGCTAC  TCCCCGAAAC  GTACCAATAG  CAAGAAAAGT  2750
ATCCATAATG  AGAGCAAATG  GCAAAAATAA  CACGGTCCTG  CGGGAATCTC  2800
GCAGAACCGT  AGACTAGGAA  TGCCAGCCCC  CCAAATTGAT  GTGACCCTGC  2850
CCCGGGTTAG  ACAATGATAA  AATGCGCTGG  CCTTTATTTT  CTGTGTTGGG  2900
TTTTCCCTTG  CCTTATGGGC  TGAAGTGTTC  TCTAGAATTT  AGCAGGTCAC  2950
ACTGAGGGGA  TTCCAGTTTA  ACTGTGGGTC  CCTCCTCCTC  TCCTACCCCA  3000
TCCCTGCCCT  TCCAGAGAAT  AACAGGAAGC  CTTCCTTTTT  TTTTTTTTT   3050
AAGTGCTATG  CAAAAGAGAC  ATCTTTAACA  GAGTCCTGTT  ACTATGGTAA  3100
CATTTGCTT   TCTGAATTGG  GAGGAAATAA  AAATTGTAAT  GACAGCATTT  3150
GAAGGTTCTC  AGACCTCCAG  TGAGTACCTG  CAAAAATGAG  TTGTCACAGA  3200
GATTATTCCC  TACTTCTCAA  ACCTGAAAAT  GATGTTGGTT  CGATGTGTGT  3250
GTGTGTGTAT  GAGTGGGTGT  GTGGTACATG  TGTGTACATA  TATGTATAAT  3300
ATATATCTCC  AGTATATATT  ATATATATCT  ATATCATATT  TCTGTGGAGG  3350
GTTGCCATGG  CAATCAACTG  CAGTACATAT  GTAGTTCTTT  CCATCACCCT  3400
AACCTCTCCT  GCGCATTCAC  ACAAGAGTTT  CTTGTAAGCC  ATCAAAAGTT  3450
AATTCTAGGG  GGAGAGGGAT  GAGGCGGGGA  GACATGGGAA  ACCGTCTGAT  3500
TTTAATGAAA  TCAAATGTCT  GTGTCATCGG  TTGGCTACGT  TTTGGTTCTA  3550
TGCTAAACTG  TGAAGAATCG  GATGAATTGA  TGAAGAGTTG  AGTTACCTGC  3600
AACCCATTGA  GAAGTGTCCT  GTGCGTCTGT  TTTGTGTCTG  GTGCAGAAAA  3650
TGACAATCTA  CCAACTGTCC  CCTTATTTGG  AGTTGGTTCA  GCTTTGGAAA  3700
GTTACTGTAA  ATGCCTTGCT  TGTATTATCA  TCCCTAGTCA  CCTGACTTCG  3750
GAGCTTGCAC  CATCGTGTTT  TAAGTGAAGA  CGCTGTAAAT  AGGTTCAGAT  3800
CTTACCGTCT  ATGGATTCGG  GTGTTACAGT  AGCCTTATTC  ACCTTTTAA   3850
TAAAAATACA  CATGAAAACG  AGACAGTAAT  GGCTTTTCTT  ACCCAGATTG  3900
```

```
TGTACATAGA GCAATGTTGG TTTTTTATAA AGTCTAAGCA AGATGTTTTG    3950

TATAAAATCT GAATTTTGCA ATGTATTTAG CTACAGCTTT TAACGGCAGT    4000

GTCATCCCCT TTGCACTGTA ATGAGGAAAA AAAAAAGGTA TAAAAGGTTG    4050

CCAAATTGCT GCATATTTGT GCCGTAATTA TGTACCATGA ATATTTATTT    4100

AATTCGTTG  TCCAATTTGT AAGTAACACA GTATTATGCT TGAGTTATAA    4150

ATATTTTTC  TTTGTTTTAT TTAATAGCC  TGTCATAGGT TTTTTTTAA     4200

TCTGCTTTAG TTCCACATGA CAGTTAAGCC CCAGAAATGA GATCCGAGCA    4250

GCCACATTCC ACGTCTGTTT CAAAATGAAT TTGTTCTTAA AAAAAATAAA    4300

ATATTTTTT  CCTATGGAAA AAAAAAAAA  AAGGGCGGCC GC            4342
```

( 2 ) INFORMATION FOR SEQ ID NO:2:

( i ) SEQUENCE CHARACTERISTICS:
    ( A ) LENGTH: 336 amino acids
    ( B ) TYPE: amino acid
    ( D ) TOPOLOGY: linear ( x i ) SEQUENCE DESCRIPTION: SEQ ID NO:2:

```
Met Ala Met Ala Arg Ser Arg Arg Asp Ser Val Trp Lys Tyr Cys
 1               5                  10                  15

Trp Gly Leu Leu Met Val Leu Cys Arg Thr Ala Ile Ser Arg Ser
                20                  25                  30

Ile Val Leu Glu Pro Ile Tyr Trp Asn Ser Asn Ser Lys Phe
                35                  40                  45

Leu Pro Gly Gln Gly Leu Val Leu Tyr Pro Gln Ile Gly Asp Lys
                50                  55                  60

Leu Asp Ile Ile Cys Pro Lys Val Asp Ser Lys Thr Val Gly Gln
                65                  70                  75

Tyr Glu Tyr Tyr Lys Val Tyr Met Val Asp Lys Asp Gln Ala Asp
                80                  85                  90

Arg Cys Thr Ile Lys Lys Glu Asn Thr Pro Leu Leu Asn Cys Ala
                95                 100                 105

Arg Pro Asp Gln Asp Val Lys Phe Thr Ile Lys Phe Gln Glu Phe
               110                 115                 120

Ser Pro Asn Leu Trp Gly Leu Glu Phe Gln Lys Asn Lys Asp Tyr
               125                 130                 135

Tyr Ile Ile Ser Thr Ser Asn Gly Ser Leu Glu Gly Leu Asp Asn
               140                 145                 150

Gln Glu Gly Gly Val Cys Gln Thr Arg Ala Met Lys Ile Leu Met
               155                 160                 165

Lys Val Gly Gln Asp Ala Ser Ser Ala Gly Ser Ala Arg Asn His
               170                 175                 180

Gly Pro Thr Arg Arg Pro Glu Leu Glu Ala Gly Thr Asn Gly Arg
               185                 190                 195

Ser Ser Thr Thr Ser Pro Phe Val Lys Pro Asn Pro Gly Ser Ser
               200                 205                 210

Thr Asp Gly Asn Ser Ala Gly His Ser Gly Asn Asn Leu Leu Gly
               215                 220                 225

Ser Glu Val Ala Leu Phe Ala Gly Ile Ala Ser Gly Cys Ile Ile
               230                 235                 240

Phe Ile Val Ile Ile Ile Thr Leu Val Val Leu Leu Leu Lys Tyr
               245                 250                 255
```

| | | | | | | | | | | | | | |
|---|---|---|---|---|---|---|---|---|---|---|---|---|---|
|Arg|Arg|Arg|His|Arg<br>260|Lys|His|Ser|Pro|Gln<br>265|His|Thr|Thr|Thr|Leu<br>270|
|Ser|Leu|Ser|Thr|Leu<br>275|Ala|Thr|Pro|Lys|Arg<br>280|Gly|Gly|Asn|Asn|Asn<br>285|
|Gly|Ser|Glu|Pro|Ser<br>290|Asp|Val|Ile|Ile|Pro<br>295|Leu|Arg|Thr|Ala|Asp<br>300|
|Ser|Val|Phe|Cys|Pro<br>305|His|Tyr|Glu|Lys|Val<br>310|Ser|Gly|Asp|Tyr|Gly<br>315|
|His|Pro|Val|Tyr|Ile<br>320|Val|Gln|Glu|Met|Pro<br>325|Pro|Gln|Ser|Pro|Ala<br>330|
|Asn|Ile|Tyr|Tyr|Lys<br>335|Val<br>336| | | | | | | | | |

(2) INFORMATION FOR SEQ ID NO:3:

(i) SEQUENCE CHARACTERISTICS:
        (A) LENGTH: 1953 bases
        (B) TYPE: nucleic acid
        (C) STRANDEDNESS: single
        (D) TOPOLOGY: linear (xi) SEQUENCE DESCRIPTION: SEQ ID NO:3:

```
CTCGAGGCGC GGAGCTGGGA GTGGCTTCGC CATGGCTGTG AGAAGGGACT   50
CCGTGTGGAA GTACTGCTGG GGTGTTTTGA TGGTTTTATG CAGAACTGCG  100
ATTTCCAAAT CGATAGTTTT AGAGCCTATC TATTGGAATT CCTCGAACTC  150
CAAATTTCTA CCTGGACAAG GACTGGTACT ATACCCACAG ATAGGAGACA  200
AATTGGATAT TATTTGCCCC AAAGTGGACT CTAAAACTGT TGGCCAGTAT  250
GAATATTATA AAGTTTATAT GGTTGATAAA GACCAAGCAG ACAGATGCAC  300
TATTAAGAAG GAAAATACCC CTCTCCTCAA CTGTGCCAAA CCAGACCAAG  350
ATATCAAATT CACCATCAAG TTTCAAGAAT TCAGCCCTAA CCTCTGGGGT  400
CTAGAATTTC AGAAGAACAA AGATTATTAC ATTATATCTA CATCAAATGG  450
GTCTTTGGAG GGCCTGGATA ACCAGGAGGG AGGGGTGTGC CAGACAAGAG  500
CCATGAAGAT CCTCATGAAA GTTGGACAAG ATGCAAGTTC TGCTGGATCA  550
ACCAGGAATA AAGATCCAAC AAGACGTCCA GAACTAGAAG CTGGTACAAA  600
TGGAAGAAGT TCGACAACAA GTCCCTTTGT AAAACCAAAT CCAGGTTCTA  650
GCACAGACGG CAACAGCGCC GGACATTCGG GGAACAACAT CCTCGGTTCC  700
GAAGTGGCCT TATTTGCAGG GATTGCTTCA GGATGCATCA TCTTCATCGT  750
CATCATCATC ACGCTGGTGG TCCTCTTGCT GAAGTACCGG AGGAGACACA  800
GGAAGCACTC GCCGCAGCAC ACGACCACGC TGTCGCTCAG CACACTGGCC  850
ACACCCAAGC GCAGCGGCAA CAACAACGGC TCAGAGCCCA GTGACATTAT  900
CATCCCGCTA AGGACTGCGG ACAGCGTCTT CTGCCCTCAC TACGAGAAGG  950
TCAGCGGGGA CTACGGGCAC CCGGTGTACA TCGTCCAGGA GATGCCCCG  1000
CAGAGCCCGG CGAACATTTA CTACAAGGTC TGAGAGGGAC CCTGGTGGTA 1050
CCTGTGCTTT CCCAGAGGAC ACCTAATGTC CCGATGCCTC CCTTGAGGGT 1100
TTGAGAGCCC GCGTGCTGGA GAATTGACTG AAGCACAGCA CCGGGGGAGA 1150
GGGACACTCC TCCTCGGAAG AGCCCGTCGC GCTGGACAGC TTACCTAGTC 1200
TTGTAGCATT CGGCCTTGGT GAACACACAC GCTCCCTGGA AGCTGGAAGA 1250
CTGTGCAGAA GACGCCCATT CGGACTGCTG TGCCGCGTCC CACGTCTCCT 1300
```

```
CCTCGAAGCC ATGTGCTGCG GTCACTCAGG CCTCTGCAGA AGCCAAGGGA   1350
AGACAGTGGT TTGTGGACGA GAGGGCTGTG AGCATCCTGG CAGGTGCCCC   1400
AGGATGCCAC GCCTGGAAGG GCCGGCTTCT GCCTGGGGTG CATTTCCCCC   1450
GCAGTGCATA CCGGACTTGT CACACGGACC TCGGGCTAGT TAAGGTGTGC   1500
AAAGATCTCT AGAGTTTAGT CCTTACTGTC TCACTCGTTC TGTTACCCAG   1550
GGCTCTGCAG CACCTCACCT GAGACCTCCA CTCCACATCT GCATCACTCA   1600
TGGAACACTC ATGTCTGGAG TCCCTCCTC  CAGCCGCTGG CAACAACAGC   1650
TTCAGTCCAT GGGTAATCCG TTCATAGAAA TTGTGTTTGC TAACAAGGTG   1700
CCCTTTAGCC AGATGCTAGG CTGTCTGCGA AGAAGGCTAG GAGTTCATAG   1750
AAGGGAGTGG GGCTGGGGAA AGGGCTGGCT GCAATTGCAG CTCACTGCTG   1800
CTGCCTCTGA AACAGAAAGT TGGAAAGGAA AAAAGAAAAA AGCAATTAGG   1850
TAGCACAGCA CTTTGGTTTT GCTGAGATCG AAGAGGCCAG TAGGAGACAC   1900
GACAGCACAC ACAGTGGATT CCAGTGCATG GGGAGGCGGT CGACGAGCTC   1950
GAG 1953
```

( 2 ) INFORMATION FOR SEQ ID NO:4:

( i ) SEQUENCE CHARACTERISTICS:
( A ) LENGTH: 333 amino acids
( B ) TYPE: amino acid
( D ) TOPOLOGY: linear ( x i ) SEQUENCE DESCRIPTION: SEQ ID NO:4:

```
Met Ala Val Arg Arg Asp Ser Val Trp Lys Tyr Cys Trp Gly Val
 1               5                  10                  15

Leu Met Val Leu Cys Arg Thr Ala Ile Ser Lys Ser Ile Val Leu
                20                  25                  30

Glu Pro Ile Tyr Trp Asn Ser Ser Asn Ser Lys Phe Leu Pro Gly
                35                  40                  45

Gln Gly Leu Val Leu Tyr Pro Gln Ile Gly Asp Lys Leu Asp Ile
                50                  55                  60

Ile Cys Pro Lys Val Asp Ser Lys Thr Val Gly Gln Tyr Glu Tyr
                65                  70                  75

Tyr Lys Val Tyr Met Val Asp Lys Asp Gln Ala Asp Arg Cys Thr
                80                  85                  90

Ile Lys Lys Glu Asn Thr Pro Leu Leu Asn Cys Ala Lys Pro Asp
                95                  100                 105

Gln Asp Ile Lys Phe Thr Ile Lys Phe Gln Glu Phe Ser Pro Asn
                110                 115                 120

Leu Trp Gly Leu Glu Phe Gln Lys Asn Lys Asp Tyr Tyr Ile Ile
                125                 130                 135

Ser Thr Ser Asn Gly Ser Leu Glu Gly Leu Asp Asn Gln Glu Gly
                140                 145                 150

Gly Val Cys Gln Thr Arg Ala Met Lys Ile Leu Met Lys Val Gly
                155                 160                 165

Gln Asp Ala Ser Ser Ala Gly Ser Thr Arg Asn Lys Asp Pro Thr
                170                 175                 180

Arg Arg Pro Glu Leu Glu Ala Gly Thr Asn Gly Arg Ser Ser Thr
                185                 190                 195

Thr Ser Pro Phe Val Lys Pro Asn Pro Gly Ser Ser Thr Asp Gly
                200                 205                 210
```

| | | | | | | | | | | | | |
|---|---|---|---|---|---|---|---|---|---|---|---|---|
|Asn|Ser|Ala|Gly|His 215|Ser|Gly|Asn|Asn 220|Ile|Leu|Gly|Ser|Glu Val 225|
|Ala|Leu|Phe|Ala|Gly 230|Ile|Ala|Ser|Gly|Cys 235|Ile|Ile|Phe|Ile Val 240|
|Ile|Ile|Ile|Thr|Leu 245|Val|Val|Leu|Leu|Leu 250|Lys|Tyr|Arg|Arg Arg 255|
|His|Arg|Lys|His|Ser 260|Pro|Gln|His|Thr|Thr 265|Thr|Leu|Ser|Leu Ser 270|
|Thr|Leu|Ala|Thr|Pro 275|Lys|Arg|Ser|Gly|Asn 280|Asn|Asn|Gly|Ser Glu 285|
|Pro|Ser|Asp|Ile|Ile 290|Ile|Pro|Leu|Arg|Thr 295|Ala|Asp|Ser|Val Phe 300|
|Cys|Pro|His|Tyr|Glu 305|Lys|Val|Ser|Gly|Asp 310|Tyr|Gly|His|Pro Val 315|
|Tyr|Ile|Val|Gln|Glu 320|Met|Pro|Pro|Gln|Ser 325|Pro|Ala|Asn|Ile Tyr 330|
|Tyr|Lys|Val 333| | | | | | | | | | | |

( 2 ) INFORMATION FOR SEQ ID NO:5:

( i ) SEQUENCE CHARACTERISTICS:
        ( A ) LENGTH: 3969 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TCGGCGTCCA  CCCGCCCAGG  GAGAGTCAGA  CCTGGGGGGG  CGAGGGCCCC   50
CCAAACTCAG  TTCGGATCCT  ACCCGAGTGA  GGCGGCGCCA  TGGAGCTCCG  100
GGTGCTGCTC  TGCTGGGCTT  CGTTGGCCGC  AGCTTTGGAA  GAGACCCTGC  150
TGAACACAAA  ATTGGAAACT  GCTGATCTGA  AGTGGGTGAC  ATTCCCTCAG  200
GTGGACGGGC  AGTGGGAGGA  ACTGAGCGGC  CTGGATGAGG  AACAGCACAG  250
CGTGCGCACC  TACGAAGTGT  GTGACGTGCA  GCGTGCCCCG  GGCCAGGCCC  300
ACTGGCTTCG  CACAGGTTGG  GTCCACGGC   GGGGCGCCGT  CCACGTGTAC  350
GCCACGCTGC  GCTTCACCAT  GCTCGAGTGC  CTGTCCCTGC  CTCGGGCTGG  400
GCGCTCCTGC  AAGGAGACCT  TCACCGTCTT  CTACTATGAG  AGCGATGCGG  450
ACACGGCCAC  GGCCCTCACG  CCAGCCTGGA  TGGAGAACCC  CTACATCAAG  500
GTGGACACGG  TGGCCGCGGA  GCATCTCACC  CGGAAGCGCC  CTGGGGCCGA  550
GGCCACCGGG  AAGGTGAATG  TCAAGACGCT  GCGTCTGGGA  CCGCTCAGCA  600
AGGCTGGCTT  CTACCTGGCC  TTCCAGGACC  AGGGTGCCTG  CATGGCCCTG  650
CTATCCCTGC  ACCTCTTCTA  CAAAAAGTGC  GCCCAGCTGA  CTGTGAACCT  700
GACTCGATTC  CCGGAGACTG  TGCCTCGGGA  GCTGGTTGTG  CCCGTGGCCG  750
GTAGCTGCGT  GGTGGATGCC  GTCCCCGCCC  CTGGCCCCAG  CCCCAGCCTC  800
TACTGCCGTG  AGGATGGCCA  GTGGGCCGAA  CAGCCGGTCA  CGGGCTGCAG  850
CTGTGCTCCG  GGGTTCGAGG  CAGCTGAGGG  AACACCAAG   TGCCGAGCCT  900
GTGCCCAGGG  CACCTTCAAG  CCCCTGTCAG  GAGAAGGGTC  CTGCCAGCCA  950
TGCCCAGCCA  ATAGCCACTC  TAACACCATT  GGATCAGCCG  TCTGCCAGTG 1000
CCGCGTCGGG  TACTTCCGGG  CACGCACAGA  CCCCCGGGGT  GCACCCTGCA 1050
```

-continued

```
CCACCCCTCC TTCGGCTCCG CGGAGCGTGG TTTCCCGCCT GAACGGCTCC 1100
TCCCTGCACC TGGAATGGAG TGCCCCCCTG GAGTCTGGTG GCCGAGAGGA 1150
CCTCACCTAC GCCCTCCGCT GCCGGGAGTG CCGACCCGGA GGCTCCTGTG 1200
CGCCCTGCGG GGGAGACCTG ACTTTTGACC CCGGCCCCCG GGACCTGGTG 1250
GAGCCCTGGG TGGTGGTTCG AGGGCTACGT CCTGACTTCA CCTATACCTT 1300
TGAGGTCACT GCATTGAACG GGTATCCTC CTTAGCCACG GGGCCCGTCC 1350
CATTTGAGCC TGTCAATGTC ACCACTGACC GAGAGGTACC TCCTGCAGTG 1400
TCTGACATCC GGGTGACGCG GTCCTCACCC AGCAGCTTGA GCCTGGCCTG 1450
GGCTGTTCCC CGGGCACCCA GTGGGGCTGT GCTGGACTAC GAGGTCAAAT 1500
ACCATGAGAA GGGCGCCGAG GGTCCCAGCA GCGTGCGGTT CCTGAAGACG 1550
TCAGAAAACC GGGCAGAGCT GCGGGGGCTG AAGCGGGGAG CCAGCTACCT 1600
GGTGCAGGTA CGGGCGCGCT CTGAGGCCGG CTACGGGCCC TTCGGCCAGG 1650
AACATCACAG CCAGACCCAA CTGGATGAGA GCGAGGGCTG GCGGGAGCAG 1700
CTGGCCCTGA TTGCGGGCAC GGCAGTCGTG GGTGTGGTCC TGGTCCTGGT 1750
GGTCATTGTG GTCGCAGTTC TCTGCCTCAG GAAGCAGAGC AATGGGAGAG 1800
AAGCAGAATA TTCGGACAAA CACGGACAGT ATCTCATCGG ACATGGTACT 1850
AAGGTCTACA TCGACCCCTT CACTTATGAA GACCCTAATG AGGCTGTGAG 1900
GGAATTTGCA AAAGAGATCG ATGTCTCCTA CGTCAAGATT GAAGAGGTGA 1950
TTGGTGCAGG TGAGTTTGGC GAGGTGTGCC GGGGCGGCT CAAGGCCCCA 2000
GGGAAGAAGG AGAGCTGTGT GGCAATCAAG ACCCTGAAGG GTGGCTACAC 2050
GGAGCGGCAG CGGCGTGAGT TTCTGAGCGA GGCCTCCATC ATGGGCCAGT 2100
TCGAGCACCC CAATATCATC CGCCTGGAGG GCGTGGTCAC CAACAGCATG 2150
CCCGTCATGA TTCTCACAGA GTTCATGGAG AACGGCGCCC TGGACTCCTT 2200
CCTGCGGCTA AACGACGGAC AGTTCACAGT CATCCAGCTC GTGGGCATGC 2250
TGCGGGGCAT CGCCTCGGGC ATGCGGTACC TTGCCGAGAT GAGCTACGTC 2300
CACCGAGACC TGGCTGCTCG CAACATCCTA GTCAACAGCA ACCTCGTCTG 2350
CAAAGTGTCT GACTTTGGCC TTTCCCGATT CCTGGAGGAG AACTCTTCCG 2400
ATCCCACCTA CACGAGCTCC CTGGGAGGAA AGATTCCCAT CCGATGGACT 2450
GCCCCGGAGG CCATTGCCTT CCGGAAGTTC ACTTCCGCCA GTGATGCCTG 2500
GAGTTACGGG ATTGTGATGT GGGAGGTGAT GTCATTTGGG AGAGGCCGT 2550
ACTGGGACAT GAGCAATCAG GACGTGATCA ATGCCATTGA ACAGGACTAC 2600
CGGCTGCCCC CGCCCCAGA CTGTCCCACC TCCTCCACC AGCTCATGCT 2650
GGACTGTTGG CAGAAAGACC GGAATGCCCG GCCCCGCTTC CCCCAGGTGG 2700
TCAGCGCCCT GGACAAGATG ATCCGGAACC CCGCCAGCCT CAAAATCGTG 2750
GCCCGGGAGA ATGGCGGGGC CTCACACCCT CTCCTGGACC AGCGGCAGCC 2800
TCACTACTCA GCTTTTGGCT CTGTGGGCGA GTGGCTTCGG GCCATCAAAA 2850
TGGGAAGATA CGAAGAAAGT TTCGCAGCCG CTGGCTTTGG CTCCTTCGAG 2900
CTGGTCAGCC AGATCTCTGC TGAGGACCTG CTCCGAATCG GAGTCACTCT 2950
GGCGGGACAC CAGAAGAAAA TCTTGGCCAG TGTCCAGCAC ATGAAGTCCC 3000
AGGCCAAGCC GGGAACCCCG GGTGGGACAG GAGGACCGGC CCCGCAGTAC 3050
```

```
TGACCTGCAG GAACTCCCCA CCCCAGGGAC ACCGCCTCCC CATTTTCCGG 3100
GGCAGAGTGG GGACTCACAG AGGCCCCCAG CCCTGTGCCC CGCTGGATTG 3150
CACTTTGAGC CCGTGGGGTG AGGAGTTGGC AATTTGGAGA GACAGGATTT 3200
GGGGGTTCTG CCATAATAGG AGGGGAAAAT CACCCCCCAG CCACCTCGGG 3250
GAACTCCAGA CCAAGGGTGA GGGCGCCTTT CCCTCAGGAC TGGGTGTGAC 3300
CAGAGGAAAA GGAAGTGCCC AACATCTCCC AGCCTCCCCA GGTGCCCCCC 3350
TCACCTTGAT GGGTGCGTTC CCGCAGACCA AAGAGAGTGT GACTCCCTTG 3400
CCAGCTCCAG AGTGGGGGGG CTGTCCCAGG GGGCAAGAAG GGGTGTCAGG 3450
GCCCAGTGAC AAAATCATTG GGGTTTGTAG TCCCAACTTG CTGCTGTCAC 3500
CACCAAACTC AATCATTTTT TTCCCTTGTA AATGCCCCTC CCCCAGCTGC 3550
TGCCTTCATA TTGAAGGTTT TTGAGTTTTG TTTTGGTCT TAATTTTCT 3600
CCCCGTTCCC TTTTTGTTTC TTCGTTTTGT TTTCTACCG TCCTTGTCAT 3650
AACTTTGTGT TGGAGGGAAC CTGTTTCACT ATGGCCTCCT TTGCCCAAGT 3700
TGAAACAGGG GCCCATCATC ATGTCTGTTT CCAGAACAGT GCCTTGGTCA 3750
TCCCACATCC CCGGACCCCG CCTGGGACCC CCAAGCTGTG TCCTATGAAG 3800
GGGTGTGGGG TGAGGTAGTG AAAAGGGCGG TAGTTGGTGG TGGAACCCAG 3850
AAACGGACGC CGGTGCTTGG AGGGGTTCTT AAATTATATT TAAAAAGTA 3900
ACTTTTTGTA TAAATAAAAG AAAATGGGAC GTGTCCAGC TCCAGGGGTA 3950
AAAAAAAAAA AAAAAAAA 3969
```

( 2 ) INFORMATION FOR SEQ ID NO:6:

( i ) SEQUENCE CHARACTERISTICS:
( A ) LENGTH: 987 amino acids
( B ) TYPE: amino acid
( D ) TOPOLOGY: linear ( x i ) SEQUENCE DESCRIPTION: SEQ ID NO:6:

```
Met Glu Leu Arg Val Leu Leu Cys Trp Ala Ser Leu Ala Ala Ala
 1               5                  10                  15

Leu Glu Glu Thr Leu Leu Asn Thr Lys Leu Glu Thr Ala Asp Leu
                20                  25                  30

Lys Trp Val Thr Phe Pro Gln Val Asp Gly Gln Trp Glu Glu Leu
                35                  40                  45

Ser Gly Leu Asp Glu Glu Gln His Ser Val Arg Thr Tyr Glu Val
                50                  55                  60

Cys Asp Val Gln Arg Ala Pro Gly Gln Ala His Trp Leu Arg Thr
                65                  70                  75

Gly Trp Val Pro Arg Arg Gly Ala Val His Val Tyr Ala Thr Leu
                80                  85                  90

Arg Phe Thr Met Leu Glu Cys Leu Ser Leu Pro Arg Ala Gly Arg
                95                 100                 105

Ser Cys Lys Glu Thr Phe Thr Val Phe Tyr Tyr Glu Ser Asp Ala
               110                 115                 120

Asp Thr Ala Thr Ala Leu Thr Pro Ala Trp Met Glu Asn Pro Tyr
               125                 130                 135

Ile Lys Val Asp Thr Val Ala Ala Glu His Leu Thr Arg Lys Arg
               140                 145                 150

Pro Gly Ala Glu Ala Thr Gly Lys Val Asn Val Lys Thr Leu Arg
```

|     |     |     |     | 155 |     |     |     | 160 |     |     |     | 165 |
|---|---|---|---|---|---|---|---|---|---|---|---|---|

Leu Gly Pro Leu Ser Lys Ala Gly Phe Tyr Leu Ala Phe Gln Asp
                170                 175                 180

Gln Gly Ala Cys Met Ala Leu Leu Ser Leu His Leu Phe Tyr Lys
                185                 190                 195

Lys Cys Ala Gln Leu Thr Val Asn Leu Thr Arg Phe Pro Glu Thr
                200                 205                 210

Val Pro Arg Glu Leu Val Val Pro Val Ala Gly Ser Cys Val Val
                215                 220                 225

Asp Ala Val Pro Ala Pro Gly Pro Ser Pro Ser Leu Tyr Cys Arg
                230                 235                 240

Glu Asp Gly Gln Trp Ala Glu Gln Pro Val Thr Gly Cys Ser Cys
                245                 250                 255

Ala Pro Gly Phe Glu Ala Ala Glu Gly Asn Thr Lys Cys Arg Ala
                260                 265                 270

Cys Ala Gln Gly Thr Phe Lys Pro Leu Ser Gly Glu Gly Ser Cys
                275                 280                 285

Gln Pro Cys Pro Ala Asn Ser His Ser Asn Thr Ile Gly Ser Ala
                290                 295                 300

Val Cys Gln Cys Arg Val Gly Tyr Phe Arg Ala Arg Thr Asp Pro
                305                 310                 315

Arg Gly Ala Pro Cys Thr Thr Pro Pro Ser Ala Pro Arg Ser Val
                320                 325                 330

Val Ser Arg Leu Asn Gly Ser Ser Leu His Leu Glu Trp Ser Ala
                335                 340                 345

Pro Leu Glu Ser Gly Gly Arg Glu Asp Leu Thr Tyr Ala Leu Arg
                350                 355                 360

Cys Arg Glu Cys Arg Pro Gly Gly Ser Cys Ala Pro Cys Gly Gly
                365                 370                 375

Asp Leu Thr Phe Asp Pro Gly Pro Arg Asp Leu Val Glu Pro Trp
                380                 385                 390

Val Val Val Arg Gly Leu Arg Pro Asp Phe Thr Tyr Thr Phe Glu
                395                 400                 405

Val Thr Ala Leu Asn Gly Val Ser Ser Leu Ala Thr Gly Pro Val
                410                 415                 420

Pro Phe Glu Pro Val Asn Val Thr Thr Asp Arg Glu Val Pro Pro
                425                 430                 435

Ala Val Ser Asp Ile Arg Val Thr Arg Ser Ser Pro Ser Ser Leu
                440                 445                 450

Ser Leu Ala Trp Ala Val Pro Arg Ala Pro Ser Gly Ala Val Leu
                455                 460                 465

Asp Tyr Glu Val Lys Tyr His Glu Lys Gly Ala Glu Gly Pro Ser
                470                 475                 480

Ser Val Arg Phe Leu Lys Thr Ser Glu Asn Arg Ala Glu Leu Arg
                485                 490                 495

Gly Leu Lys Arg Gly Ala Ser Tyr Leu Val Gln Val Arg Ala Arg
                500                 505                 510

Ser Glu Ala Gly Tyr Gly Pro Phe Gly Gln Glu His His Ser Gln
                515                 520                 525

Thr Gln Leu Asp Glu Ser Glu Gly Trp Arg Glu Gln Leu Ala Leu
                530                 535                 540

Ile Ala Gly Thr Ala Val Val Gly Val Val Leu Val Leu Val Val
                545                 550                 555

| | | | | | | | | | | | | | | |
|---|---|---|---|---|---|---|---|---|---|---|---|---|---|---|
|Ile|Val|Val|Ala|Val 560|Leu|Cys|Leu|Arg|Lys 565|Gln|Ser|Asn|Gly|Arg 570|
|Glu|Ala|Glu|Tyr|Ser 575|Asp|Lys|His|Gly|Gln 580|Tyr|Leu|Ile|Gly|His 585|
|Gly|Thr|Lys|Val|Tyr 590|Ile|Asp|Pro|Phe|Thr 595|Tyr|Glu|Asp|Pro|Asn 600|
|Glu|Ala|Val|Arg|Glu 605|Phe|Ala|Lys|Glu|Ile 610|Asp|Val|Ser|Tyr|Val 615|
|Lys|Ile|Glu|Glu|Val 620|Ile|Gly|Ala|Gly|Glu 625|Phe|Gly|Glu|Val|Cys 630|
|Arg|Gly|Arg|Leu|Lys 635|Ala|Pro|Gly|Lys|Lys 640|Glu|Ser|Cys|Val|Ala 645|
|Ile|Lys|Thr|Leu|Lys 650|Gly|Gly|Tyr|Thr|Glu 655|Arg|Gln|Arg|Arg|Glu 660|
|Phe|Leu|Ser|Glu|Ala 665|Ser|Ile|Met|Gly|Gln 670|Phe|Glu|His|Pro|Asn 675|
|Ile|Ile|Arg|Leu|Glu 680|Gly|Val|Val|Thr|Asn 685|Ser|Met|Pro|Val|Met 690|
|Ile|Leu|Thr|Glu|Phe 695|Met|Glu|Asn|Gly|Ala 700|Leu|Asp|Ser|Phe|Leu 705|
|Arg|Leu|Asn|Asp|Gly 710|Gln|Phe|Thr|Val|Ile 715|Gln|Leu|Val|Gly|Met 720|
|Leu|Arg|Gly|Ile|Ala 725|Ser|Gly|Met|Arg|Tyr 730|Leu|Ala|Glu|Met|Ser 735|
|Tyr|Val|His|Arg|Asp 740|Leu|Ala|Ala|Arg|Asn 745|Ile|Leu|Val|Asn|Ser 750|
|Asn|Leu|Val|Cys|Lys 755|Val|Ser|Asp|Phe|Gly 760|Leu|Ser|Arg|Phe|Leu 765|
|Glu|Glu|Asn|Ser|Ser 770|Asp|Pro|Thr|Tyr|Thr 775|Ser|Ser|Leu|Gly|Gly 780|
|Lys|Ile|Pro|Ile|Arg 785|Trp|Thr|Ala|Pro|Glu 790|Ala|Ile|Ala|Phe|Arg 795|
|Lys|Phe|Thr|Ser|Ala 800|Ser|Asp|Ala|Trp|Ser 805|Tyr|Gly|Ile|Val|Met 810|
|Trp|Glu|Val|Met|Ser 815|Phe|Gly|Glu|Arg|Pro 820|Tyr|Trp|Asp|Met|Ser 825|
|Asn|Gln|Asp|Val|Ile 830|Asn|Ala|Ile|Glu|Gln 835|Asp|Tyr|Arg|Leu|Pro 840|
|Pro|Pro|Pro|Asp|Cys 845|Pro|Thr|Ser|Leu|His 850|Gln|Leu|Met|Leu|Asp 855|
|Cys|Trp|Gln|Lys|Asp 860|Arg|Asn|Ala|Arg|Pro 865|Arg|Phe|Pro|Gln|Val 870|
|Val|Ser|Ala|Leu|Asp 875|Lys|Met|Ile|Arg|Asn 880|Pro|Ala|Ser|Leu|Lys 885|
|Ile|Val|Ala|Arg|Glu 890|Asn|Gly|Gly|Ala|Ser 895|His|Pro|Leu|Leu|Asp 900|
|Gln|Arg|Gln|Pro|His 905|Tyr|Ser|Ala|Phe|Gly 910|Ser|Val|Gly|Glu|Trp 915|
|Leu|Arg|Ala|Ile|Lys 920|Met|Gly|Arg|Tyr|Glu 925|Glu|Ser|Phe|Ala|Ala 930|
|Ala|Gly|Phe|Gly|Ser 935|Phe|Glu|Leu|Val|Ser 940|Gln|Ile|Ser|Ala|Glu 945|
|Asp|Leu|Leu|Arg|Ile 950|Gly|Val|Thr|Leu|Ala 955|Gly|His|Gln|Lys|Lys 960|

```
Ile Leu Ala Ser Val Gln His Met Lys Ser Gln Ala Lys Pro Gly
             965                 970                 975

Thr Pro Gly Gly Thr Gly Gly Pro Ala Pro Gln Tyr
             980             985     987
```

( 2 ) INFORMATION FOR SEQ ID NO:7:

( i ) SEQUENCE CHARACTERISTICS:
    ( A ) LENGTH: 10 amino acids
    ( B ) TYPE: amino acid
    ( D ) TOPOLOGY: linear ( x i ) SEQUENCE DESCRIPTION: SEQ ID NO:7:

```
Asp Lys Thr His Thr Cys Pro Pro Cys Pro
 1           5                    10
```